(12) United States Patent
Behlke et al.

(10) Patent No.: US 7,135,284 B1
(45) Date of Patent: Nov. 14, 2006

(54) PRIMER EXTENSION METHODS FOR PRODUCTION OF HIGH SPECIFIC ACTIVITY NUCLEIC ACID PROBES

(75) Inventors: Mark Aaron Behlke, Iowa City, IA (US); Eric Jeffrey Devor, Iowa City, IA (US); Shale Anthony James, Iowa City, IA (US); Joseph Alan Walder, Chicago, IL (US)

(73) Assignee: Integrated DNA Technologies, Inc., Skokie, IL (US)

( * ) Notice: Subject to any disclaimer, the term of this patent is extended or adjusted under 35 U.S.C. 154(b) by 0 days.

(21) Appl. No.: 09/497,943

(22) Filed: Feb. 4, 2000

Related U.S. Application Data

(60) Provisional application No. 60/118,721, filed on Feb. 5, 1999.

(51) Int. Cl.
*C12Q 1/68* (2006.01)
*C12P 19/34* (2006.01)
*C07H 21/04* (2006.01)
*C07H 21/02* (2006.01)

(52) U.S. Cl. .................... 435/6; 435/91.1; 435/183; 435/287.2; 536/23.1; 536/24.3; 536/24.33

(58) Field of Classification Search .................. 435/6, 435/91.1, 91.2, 183, 287.2; 536/23.1, 24.31, 536/24.33, 24, 3
See application file for complete search history.

(56) References Cited

U.S. PATENT DOCUMENTS

| | | | |
|---|---|---|---|
| 4,683,202 A | | 7/1987 | Mullis |
| 4,808,520 A | | 2/1989 | Dattagupta et al. |
| 5,403,711 A | | 4/1995 | Walder et al. |
| 5,538,872 A | | 7/1996 | Bahl et al. |
| 5,599,708 A | * | 2/1997 | Mundy et al. ............... 435/331 |
| 5,614,389 A | * | 3/1997 | Auerbach .................. 435/91.2 |
| 5,710,028 A | * | 1/1998 | Eyal et al. ................. 435/91.1 |
| 5,882,856 A | * | 3/1999 | Shuber ........................... 435/6 |
| 5,989,871 A | * | 11/1999 | Grossman et al. ......... 435/91.1 |
| 6,248,568 B1 | * | 6/2001 | Khan et al. ................. 435/91.1 |
| 2004/0121377 A1 | * | 6/2004 | Ishii et al. ..................... 435/6 |

FOREIGN PATENT DOCUMENTS

| | | |
|---|---|---|
| WO | WO 93/05175 A1 * | 3/1993 |
| WO | WO-94/02640 | 2/1994 |
| WO | WO-98/30719 | 7/1998 |

OTHER PUBLICATIONS

Caruthers et al., 1987, "Chemical synthesis of deoxyoligonucleotides by the phosphoramidite method", Methods Enzymol. 154:287-313.

Chaconas and van de Sande, 1980, "5'-$^{32}$P labeling of RNA and DNA restriction fragmnets", Methods Enzymol. 65:75-88.

Clontech Catalog 95/96, Label-On Reagents, p. 198.

Clontech Catalog 95/96, Oligo-AP Labeling Kit, p. 208.

Clontech Catalog 95/96, Virtual Nucleotide Reagents, p. 195.

Gilfillan et al., 1995, "Mice lacking terminal deoxynucleotidyl transferase: adult mice with a fetal antigen receptor repertoire", Immunol Rev. 148:201-19.

Langer et al, 1981, "Enzymatic synthesis of biotinylated polynucleotides: novel nucleic acid affinity probes", Proc. Natl. Acad. Sci. USA 78:6633-6637.

Moore, 1981, "Pancreatic Dnase", *The Enzymes* (Academic Press, San Diego) pp. 281-298.

Rock et al., 1994, "CDR3 length in antigen-specific immune receptors", J Exp Med. 179(1):323-8.

Shchepinov et al., 1997, "Oligonucleotide dendrimers: synthesis and use as polylabelled DNA probes", Nucleic Acids Res. 25(22):4447-54.

Studencki and Wallace, 1984, "Allele-specific hybridization using oligonucleotide probes of very high specific activity: discrimination of the human beta A- and beta S-globin genes", DNA 3(1):7-15.

Uhlenbeck and Gumport, 1982, "T4 RNA ligase", The Enzymes (Academic Press, San Diego) pp. 31-60.

Ullrich et al., 1984, "Human epidermal growth factor receptor cDNA sequence and aberrant expression of the amplified gene in A431 epidermoid carcinoma cells", Nature 309(5967):418-25.

USB Molecular Biology Reagents/Protocols 1992, Bacterial Alkaline Phosphatase, p. 84.

USB Molecular Biology Reagents/Protocols 1992, Calf Intestine Alkaline Phosphatase, p. 86.

USB Molecular Biology Reagents/Protocols 1992, Exonuclease III, p. 101.

USB Molecular Biology Reagents/Protocols 1992, T4 Polynucleotide Kinase (Cloned) p. 110.

(Continued)

*Primary Examiner*—Bradley L. Sisson
(74) *Attorney, Agent, or Firm*—Michael Best & Friedrich LLP

(57) ABSTRACT

The present invention provides novel nucleic acid labeling techniques that generate nucleic acid probes with specific activities at least ten fold higher than the levels obtained using standard labeling methods. Specifically, the methods of the invention provides methods of producing nucleic acid probes that each comprises multiple labeled nucleotides. The methods can be used to generate RNA, DNA or hybrid probes. The invention also provides reaction mixtures and kits for the practice of the methods of the invention and compositions comprising the probes generated according to the methods of the invention.

23 Claims, 9 Drawing Sheets

OTHER PUBLICATIONS

Figure 3:
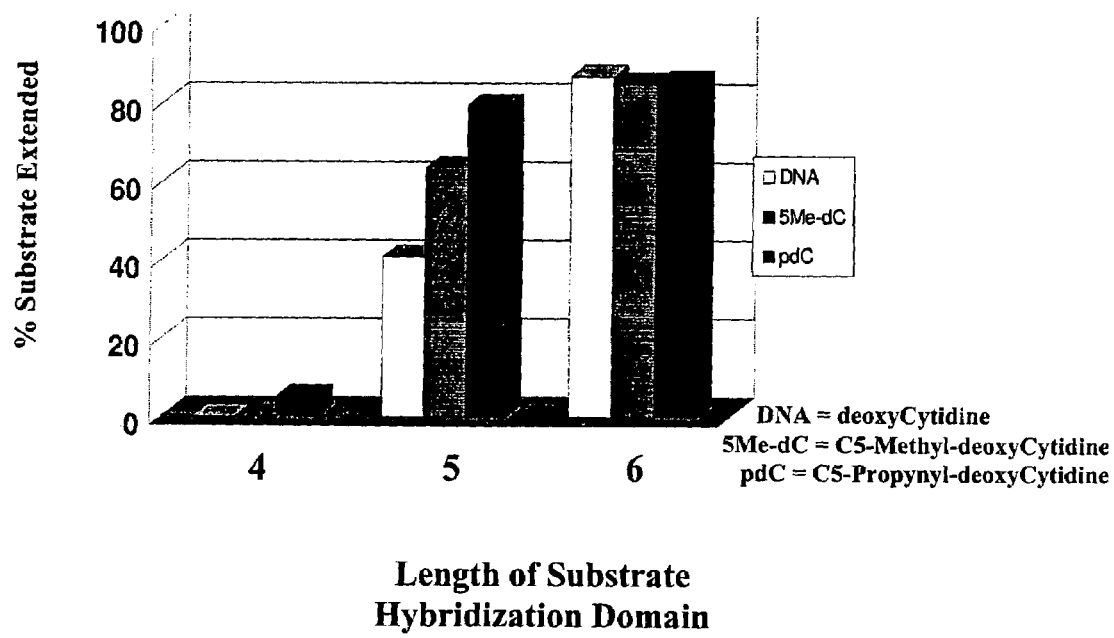

USB Molecular Biology Reagents/Protocols 1992, DNA Polymerase I, p. 133.

USB Molecular Biology Reagents/Protocols 1992, Poly(A) Polymerase, p. 138.

USB Molecular Biology Reagents/Protocols 1992, T3 RNA Polymerase (Cloned), p. 161.

USB Molecular Biology Reagents/Protocols 1992, T7 RNA Polymerase, p. 162.

USB Molecular Biology Reagents/Protocols 1992, terminal Deoxynucleotidyl Transferase, p. 184.

Wilcheck and Bayer, 1988, "The avidin-biotin complex in bioanalytical applications", Anal. Biochem. 171:1-32.

Maag and Schmidt, 1994, "Oligodeoxynucleotide probes with multiple labels linked to the 4'-position of thymidine monomers: excellent duplex stability and detection sensitivity", Tetrahedron Lett. 35(35):6449-52.

Bathum et al., A Dual Label Oligonucleotide Ligation Assay for Detection of the CYP2C19*1, CYP2C19*2, and CYP2C19*3 Alleles Involving Time-Resolved Fluorometry, Therapeutic Drug Monitoring, 1998, 1-6, 20.

Ahern, Biochemical, Reagent Kits Offer Scientists Good Return on Investment, http://www.the-scientist.library.upenn.edu/yr1995/july/tools_950724.html.

Kao et al., A Simple and Efficient Method to Reduce Nontemplated Nucleotide Addition at the 3' terminus of RNAs Transcribed by T7 RNA Polymerase, RNA, 1999, 1268-1272, 5.

Orgel, Adding to the Genetic Alphab t, Natur , Jan. 4, 1990, 18-20, vol. 343.

Piccirilli, Enzymatic Incorporation of a New Base Pair Into DNA and RNA Extends th Genetic Alphabet, Nature, Jan. 4, 1990, 33-37, vol. 343.

* cited by examiner

A) Design and Synthesis of Nucleic Acids (oligonucleotides):
   i) *Substrate Nucleic Acid*

5' Specific Sequence Domain
   (TARGET BINDING DOMAIN)

Universal TEMPLATE
   HYBRIDIZATION DOMAIN
   (same for all probes)

ii) *Template Nucleic Acid*

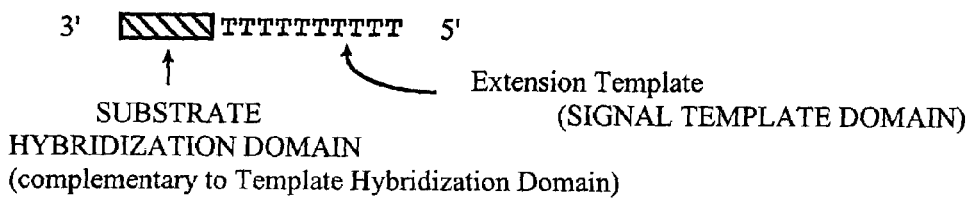

SUBSTRATE
   HYBRIDIZATION DOMAIN
   (complementary to Template Hybridization Domain)

Extension Template
   (SIGNAL TEMPLATE DOMAIN)

B) Anneal Substrate + Template Nucleic Acids in Buffer (10 minutes)

C) Labeling / Extension Reaction (1 hour)
   Add DNA Polymerase + α-$^{32}$P-dATP [*A]

Labeled Substrate
   Nucleic Acid
   (PROBE)

D) Remove Unincorporated Label using Column Chromatography (10 minutes)
   Optional: Remove Template and more highly purify Probe using PAGE (2 hour gel + elute)

FIG. 1

A) Substrate and Template Nucleic Acids
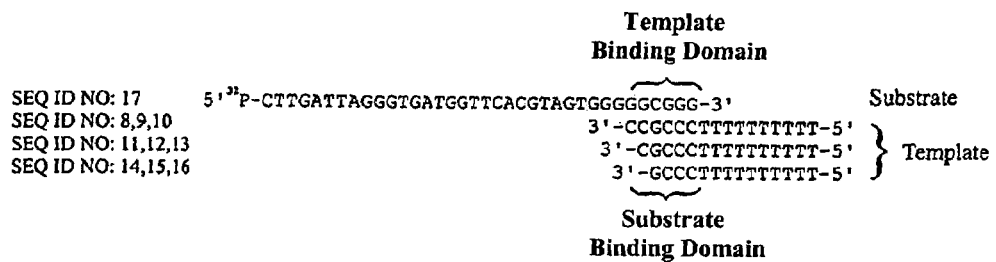
B) PAGE analysis of reaction products
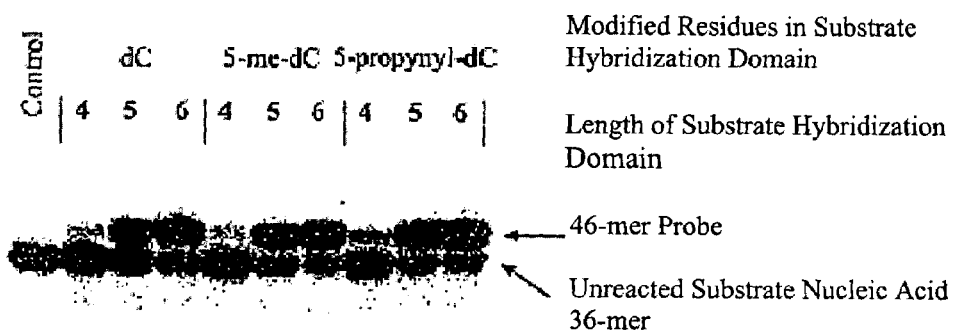
FIG. 2 pGreen Lantern™-1 Probes

Kinase Labeled Probe

5'-$^{32}$P-CTTGATTAGGGTGATGGTTCACGTAGTGGGGGCGGG-3'

High Specific Activity Tailed Probe

5'-CTTGATTAGGGTGATGGTTCACGTAGTGGGGGCGGG*A*A*A*A*A*A*A*A*A*A-3'

∗ = $^{32}$P  (10 total)

FIG. 4A

β-Actin Probes

Kinase Labeled Probe

5'-$^{32}$P-GCCCAGGAAGGAAGGCTGGAAGAGTGCCTCGGCGGG-3'

High Specific Activity Tailed Probe

5'-GCCCAGGAAGGAAGGCTGGAAGAGTGCCTCGGCGGG*A*A*A*A*A*A*A*A*A*A-3'

* = $^{32}$P (10 total)

FIG. 5A

Substrate Nucleic Acids and Reaction Products

SEQ ID NO: 21   DNA Substrate Nucleic Acid

5'-$^{32}$P-GCCCAGGAAGGAAGGCTGGAAGAGTGCCTCGGCGGG-3'

SEQ ID NO: 22   DNA Reaction Product

5'-$^{32}$P-GCCCAGGAAGGAAGGCTGGAAGAGTGCCTCGGCGGGAAAAAAAAAA-3'

SEQ ID NO: 24   RNA Substrate Nucleic Acid

5'-$^{32}$P-cugggcauggaguccuguggcauccacgaaacuaccuucaggcggg-3'

SEQ ID NO: 25   RNA Reaction Product

5'-$^{32}$P-cugggcauggaguccuguggcauccacgaaacuaccuucaggcgggAAAAAAAAAA-3'

FIG. 6A

PAGE analysis of Reaction Products

PRIMER EXTENSION METHODS FOR PRODUCTION OF HIGH SPECIFIC ACTIVITY NUCLEIC ACID PROBES This application claims priority, under 35 U.S.C. § 119(e), of United States Provisional Patent Application No. 60/118,721, filed Feb. 5, 1999, which is incorporated by reference herein in its entirety.

1. INTRODUCTION

The present invention relates to nucleic acids, complexes, reaction mixtures, kits, and nucleic acid probe labeling techniques designed to increase the probe specific activity many-fold above the levels obtained using existing labeling techniques. Specifically, the present invention relates to methods of incorporating a plurality of labels into a single probe molecule. The present invention further relates to nucleic acid compositions labeled by such methods and to kits for performing the labeling methods of the invention.

2. BACKGROUND OF THE INVENTION

Oligonucleotides are DNA, RNA or DNA/RNA hybrid molecules that in general are relatively short, synthetic, and single stranded. Synthetic oligonucleotides are inexpensive, readily available, and can be made for any desired sequence. These molecules are often labeled with molecular tracers to follow their presence in various assays. Such labeled molecules are commonly referred to as "probes". The labeled oligonucleotide can be used as a hybridization probe to identify nucleic acids and studying the binding of proteins and other molecules to the probe. The results obtained using such assays depend in large part upon the specific activity of the probe. In general, probes of high specific activity that can be generated in a controllable and reproducible manner are most desirable.

Common nucleic acid labels currently include groups containing radioactive atoms such as $^{32}P$ or $^{35}S$, biotin, fluorescent molecules (e.g. fluorescein and rhodamine derivatives) and enzymes whose activity is detectable, for example, as a result of catalyzing a reaction that produces a fluorescing or colorimetric reagent (e.g. horseradish peroxidase and alkaline phosphatase). In addition, nucleotide analogs conjugated to haptens (e.g. biotin, digoxigenin, etc.) may be used to label the nucleic acid. A hapten is subsequently recognized by a high affinity binding ligand (e.g., streptavidin) or an antibody, that is conjugated to a fluorescent marker or enzyme reagent for detection of the nucleic acid.

Generally, polynucleotide kinase (PNK) is used to radiolabel oligonucleotides with $\gamma$-$^{32}P$-ATP, in particular at the 5' phosphate. If there is no phosphate group present on the 5' end of a nucleic acid molecule, PNK can add a radiolabeled phosphate to the free 5'hydroxyl group of the nucleic acid. Alternatively, if a 5' phosphate is present, PNK can remove the non-radioactive 5' phosphate and replace it with a radiolabeled phosphate in an exchange reaction. However, in either an addition or exchange reaction, the resulting labeled nucleic acid has only a single $^{32}P$ label per nucleic acid molecule. No more than one $^{32}P$ label can be introduced per nucleic acid molecule by PNK.

The use of PNK is also limited, moreover, because the enzyme is not completely efficient in the addition reaction and even less efficient in the exchange reaction. This low efficiency can result in variable incorporation of radiolabel and a diminished specific activity measured in counts per minute (cpm) per micromole of DNA or RNA substrate. Because of the inefficiency of the PNK, the enzyme reaction results leaves residual unlabeled nucleic acids. These unlabeled ("cold") nucleic acids cannot be purified away from the radiolabeled ("hot") nucleic acids because they have nearly identical chemical and physical properties. The labeled nucleic acid differs from the unlabeled molecule by the presence of only one additional phosphate group. The cold nucleic acid will then compete with the hot nucleic acid when the labeled nucleic acid is used in a practical application, e.g., binding to a target molecule, diminishing the probe's effectiveness.

In addition, because the unlabeled nucleic acid cannot be removed, the precise specific activity of the product generally cannot be determined. Usually, the quantity of oligonucleotide labeled is too small to measure the amount of product directly recovered from the reaction, e.g., by U.V. absorbence. Therefore, specific activity can only be estimated, either based on an assumption of the efficiency of recovery of the labeled nucleic acid or the recovery of unincorporated $\alpha$-$^{32}P$-ATP.

Nucleic acid molecules can also be labeled on their free 3' hydroxyl group with a radiolabeled nucleotide, e.g., $\alpha$-$^{32}P$-dATP, using the enzyme Terminal Deoxynucleotidyl Transferase (TdT). As discussed below, TdT labeling, however, exhibits many of the same problems as PNK labeling. In particular, TdT does not efficiently label DNA, and, furthermore, the labeled nucleic acids cannot be separated from the unlabeled nucleic acids, reducing the efficiency of the method in which the labeled nucleic acid is being used.

Biologically, TdT is involved in increasing antigen receptor diversity by adding a variable number of nucleotides into chromosomal break points during the genetic rearrangement of the variable regions of immature T lymphocyte and B lymphocyte receptors (Gilfillan et al., 1995, 1 mm. Reviews 148:201). TdT adds an average of four nucleotides to chromosomal break points in vivo; however, the number of nucleotides added is extremely variable and highly dependent on local conditions (Rock et al., 1994, J. Exp. Med., 179:323). TdT also adds a variable number of nucleotides in vitro to the free 3' end of a nucleic acid probe, which makes it difficult to accurately determine the specific activity of a probe or to produce the probe in a reproducible manner. Invariably, a mixture of species is formed from which it is very difficult to isolate a unique product. Thus, this method results in a heterogeneous reaction product ranging from unlabeled to hundred-fold labeled species. Further, TdT-labeled probes with a tail that is longer than 10 or 20 residues can produce high backgrounds when hybridized to complex nucleic acid samples as a result of binding to poly A tails of mRNAs or repeats in genomic DNA.

A number of schemes have been employed to increase the specific activity and sensitivity of oligonucleotide probes without compromising their favorable hybridization properties. Ullrich et al. (1984, Nature 309:418–425) and Studencki and Wallace (1984, DNA 3:7–15) described methods in which two overlapping sequence-specific oligonucleotides are labeled in a primer extension reaction to a specific activity that can exceed 10×10$^9$ CPM/µg. While effective, these methods result in a double stranded product, require two sequence-specific custom oligonucleotides, and use two to four radiolabeled substrate deoxynucleotide triphosphates, making such approaches more expensive and less convenient than labeling with PNK. Oligonucleotides having a dendrimeric structure at the 5'-end can be synthesized and labeled to high specific activity using PNK (Shchepinov et al., 1997, Nucleic Acids Res. 25:4447–4454). However these reagents are costly and are not readily available.

Both RNA and DNA polymerase-based techniques that incorporate labeled nucleotides into nucleic acids are well known in the art (see, e.g., Ausubel et al., 1992, "Short Protocols in Molecular Biology", John Wiley & Sons, New York). For example, nick translation methods allow the preparation of uniformly labeled DNA probes for a variety of assays. Small breakages are introduced into a double stranded DNA of interest (for example by treating with DNase I), and the gaps are "filled in" using DNA polymerase in the presence of radiolabeled or non-isotopically labeled nucleotides. Alternatively, labeled probes are generated by random priming. Briefly, a double-stranded DNA of interest is denatured and the individual strands replicated in the presence of the Klenow fragment of E. coli DNA polymerase I and labeled nucleotides, using random hexamers as primers for the extension step. Alternatively, a DNA which is to be used as a probe can be generated by cutting a parent DNA with a restriction enzymes that generates a 5' overhang, and the overhang filled in using the Klenow fragment of E. coli DNA polymerase I and labeled nucleotides. Yet another method of producing a labeled DNA probe is by generating the probe by polymerase chain reaction (PCR) in the presence of labeled nucleotides.

Generally, labeled RNA probes can be produced by carrying out the transcription reaction that generates the RNA in the presence of labeled nucleotides. Such transcription reactions most commonly utilize bacteriophage RNA polymerases, such as SP6, T3, and T7.

Another scheme for labeling oligonucleotides proposed by Bahl et al. (U.S. Pat. No. 5,538,872), involves a "bridging" technique that ligates a target molecule to a signal molecule via a "bridge" molecule. The signal molecule shows no complementarity towards the target molecule, and comprises a unique 4 or more nucleotide stretch at one end and is labeled at the other end. In addition to the sequence of interest, the target molecule comprises a unique 4 or more nucleotide stretch at the end opposite to that at which the unique sequence of the signal molecule is located. The signal and target molecules are ligated by a "bridge" molecule, consisting of two specific 4 or more nucleotide sequences, one complimentary to the unique nucleotide sequence in the target molecule, and the other complimentary to the unique nucleotide sequence in the signal molecule. The target molecule, the signal molecule and the bridging molecules are allowed to hybridize, allowing the target and signal molecules to align in a directional manner. The signal and target molecules are ligated together and the result is a double stranded oligonucleotide complex that can be left as is or disassociated into the bridge and a completed probe consisting of the target and signal molecules.

Another problem associated with conventional template-based labeling methods arises when the labeled probe must be separated from the template strand. Probe techniques have been attempted to resolve this problem. For example, Dattagupta et al., U.S. Pat. No. 4,808,520, proposed a probe that is labeled by hybridizing two oligonucleotides of equal length that have regions of mutual complementarity located at the 3' ends of the oligonucleotides. One overhang is filled in with labeled nucleotides to generate a labeled probe using the other strand as a template. The template strand is not extended because it has a different nucleotide composition from the strand that is labeled, and only nucleotides required to generate the probe are added to the labeling reaction. The probe strand can then be separated from the template strand based on the differing sizes of the strands. The drawback to this method is that the template strand is designed in a sequence specific manner that depends on the oligonucleotide that is being labeled.

Clearly, therefore, a need exists for methods whereby highly purified labeled nucleic acids of high specific activity can be produced in a controllable, reproducible manner.

3. SUMMARY OF THE INVENTION

The present invention provides nucleic acids, complexes, reaction mixtures, kits, and methods for labeling nucleic acids that generate high specific activity probes. The probes produced by the methods of the invention have specific activities that are many-fold higher than the specific activities obtained using existing labeling techniques. The present invention further relates to nucleic acid compositions produced by the methods of the invention and to kits for performing the labeling methods of the invention.

The nucleic acid labeling method of the present invention generates labeled nucleic acid probes, including but not limited to radiolabeled nucleic acid probes, with at least 10-fold higher specific activity than can be obtained by traditional 5' end-labeling with PNK. Unlike other methods of radioactive tailing (i.e., TdT), the methods of the invention produce a single species of both known length and known specific activity. The reaction is highly efficient and approximately 90% of probe molecules are routinely labeled.

Specifically, the invention provides a method of labeling a nucleic acid molecule, comprising the steps of hybridizing a first nucleic acid, the Template Nucleic Acid, to a second nucleic acid, the Substrate Nucleic Acid. The Template Nucleic Acid comprises, from 3' to 5', a Substrate Hybridization Domain and a Signal Template Domain, wherein the Substrate Hybridization Domain comprises a sequence of about 5 to about 20 nucleotides and the Signal Template Domain comprises a sequence of about 5 to about 100 nucleotides. The Substrate Nucleic Acid comprises, from 3' to 5', a Template Hybridization Domain and a Target binding domain, wherein the Template Hybridization Domain comprises a sequence of about 5 to about 20 nucleotides, is not detectably labeled, and shows complementarity toward and is hybridizable to the Substrate Hybridization Domain of the Template Nucleic Acid, and the Target Binding Domain is not detectably labeled and comprises a nucleotide sequence heterologous to that of the Template Hybridization Domain of the Substrate Nucleic Acid. Upon hybridization, the Substrate Nucleic Acid is extended with a DNA polymerase in the presence of a labeled nucleotide to create a Signal Domain having a sequence which shows complementarity toward and is hybridizable to the Signal Template Domain of the Template Nucleic Acid. A Substrate Nucleic Acid comprising a Signal Domain is hereinafter called a Probe.

The labeled nucleic acid, i.e. the Probe, can also be purified from any remaining unlabeled nucleic acid, to obtain a species of very high, and precisely known, specific activity, for example by polyacrylamide gel electrophoresis ("PAGE").

The present invention particularly provides a method for obtaining labeled oligonucleotide probes comprising a plurality of labels per molecule. The plurality of labels can be of one or more species. The label can be a radiolabel, an enzyme, a hapten, or a fluorescent molecule. The precise number of labels added incorporated into the Signal Domain can be adjusted within a wide range by changing the length or sequence of the Signal Template Domain of the Template Nucleic Acid strand or by altering the ratio of labeled nucleotides in the extension reaction.

The Template Hybridization Domain of the probe does not function as a target specific hybridization sequence, but rather serves as an attachment site for the Template Nucleic Acid. This sequence is preferably added to a nucleic acid at the time the nucleic acid is synthesized. In another embodiment, the Template Hybridization Domain is added by a fill-in reaction after hybridizing to a nucleic acid molecule containing a complementary overlap sequence.

The Signal Template Domain serves as the template for the addition of labeled nucleotides. The preferred length of the Signal Template Domain is from about 5 to about 100 bases, with a length from about 10 to about 50 bases being preferred. Any sequence of bases can be employed. In a preferred embodiment, the sequence of the Signal Template Domain is oligo-dT. This provides, for example, a template for attachment of dATPs to the Substrate Nucleic Acid by primer extension catalyzed by a DNA polymerase, wherein the dATPs incorporate an appropriate label, e.g., $\alpha$-$^{32}$P-dATP.

One skilled in the art will recognize that labeled nucleotides other than dATP can be used in combination with a template other than oligo-dT. The advantages of the preferred embodiment are that poly-dA in the Signal Domain has a lower melting temperature ($T_m$) than sequences containing C or G residues, decreasing the likelihood of non-specific interactions, yet this sequence will not bind to the poly-A tail of mRNAs in hybridization reactions with cellular RNA.

Prior to labeling, the Substrate Nucleic Acid and Template Nucleic Acid strands associate by hybridizing to each other through base pairing at their corresponding binding sites, i.e., at the regions of complementarity, via the Template Hybridization Domain and the Substrate Hybridization Domain, respectively. The subsequent labeling reaction utilizes a DNA polymerase in a primer extension reaction to form a covalent attachment between the labeled nucleotides and the Substrate Nucleic Acid. DNA polymerases useful in the primer extension reaction include, but are not limited to, E. coli DNA polymerase I holoenzyme, a Klenow fragment of E. coli DNA polymerase I, T4 DNA polymerase, T7 DNA polymerase, T7 DNA polymerases, any DNA polymerase encoded by a thermophilic bacterium, including but not limited to Taq polymerase, and reverse transcriptase. The Klenow fragment of E. coli DNA Polymerase I is preferred. The enzymes can be native or recombinant and may be modified, e.g., modified to remove certain activities such as, for example, exonuclease activities. With respect to a Klenow fragment, for example, a Klenow fragment lacking the 3'-exonuclease activity of the enzyme can be utilized.

The present invention also provides a Probe nucleic acid comprising, from 3' to 5', a Signal Domain, a Template Hybridization Domain and a Target Binding Domain, wherein the Signal Domain comprises a sequence of about 5 to about 100 nucleotides of which at least two nucleotides are detectably labeled; the Template Hybridization Domain comprises a sequence of about 5 to about 20 nucleotides, and is not detectably labeled; and the Target Binding Domain is not detectably labeled and comprises a nucleotide sequence heterologous to that of the Template Hybridization Domain, and is not detectably labeled.

In one embodiment, the nucleotides which comprise the Probe nucleic acid are deoxyribonucleotides. In another embodiment, the nucleotides which comprise the Signal Domain of the Probe are deoxyribonucleotides and the nucleotides which comprise the Template Hybridization Domain and the Target Binding Domain of the Probe are ribonucleotides. In certain embodiments of the invention, the Signal Domain of the Probe comprises a sequence of about 10 to about 50 nucleotides.

The present invention provides a Probe in which the Signal Domain is at least 50%, at least 70%, at least 90% or 100% homopolymeric.

The present invention provides a Probe in which at least one nucleotide comprises a label selected from the group consisting of: $^{32}$P, $^{33}$P, $^{35}$ fluorescein, digoxigenin, biotin, Cy5, Cy3, and rhodamine.

The present invention provides a Probe in which the Template Hybridization Domain comprises a sequence of about 5 to about 10 nucleotides.

The present invention further provides a Probe in which at least 60%, at least 80% or 100% of the nucleotides of the Template Hybridization Domain comprise guanosine or cytidine or a combination thereof. In instances wherein 100% of the nucleotides of the Template Hybridization Domain comprise guanosine or cytidine, it is preferred that there be a combination of guanosine and cytidine present.

In certain embodiments of the present invention, at least 60% of the nucleotides of the Template Hybridization Domain of the Probe comprise guanosine or cytidine or a combination thereof, and the Signal Domain of the Probe is at least 50% homopolymeric.

The present invention also provides a Complex, comprising a Template Nucleic Acid comprising, from 3' to 5' a Substrate Hybridization Domain and a Signal Template Domain, wherein the Substrate Hybridization Domain comprises a sequence of about 5 to about 20 nucleotides and the Signal Template Domain comprises a sequence of about 5 to about 100 nucleotides; and a Probe nucleic acid comprising from 3' to 5' a Signal Domain, a Template Hybridization Domain and a Target Binding Domain, wherein the Signal Domain comprises a sequence of about 5 to about 100 nucleotides, which sequence shows complementarity toward and is hybridizable to the Signal Template Domain of the Template Nucleic Acid, and of which at least two nucleotides are detectably labeled; the Template Hybridization Domain comprises a sequence of about 5 to about 20 nucleotides, is not detectably labeled, and shows complementarity toward and is hybridizable to the Substrate Hybridization Domain of the Template Nucleic Acid; the Target Binding Domain is not detectably labeled and comprises a nucleotide sequence heterologous to that of the Template Hybridization Domain of the Substrate Nucleic Acid.

The present invention provides a Complex in which the nucleotides which comprise the Probe or Template Nucleic Acid are deoxyribonucleotides. The present invention provides a Complex in which the nucleotides which comprise the Template Nucleic Acid are ribonucleotides. The present invention provides a Complex in which the nucleotides which comprise the Signal Domain of the Probe are deoxyribonucleotides and the nucleotides which comprise the Template Hybridization Domain and the Target Binding Domain of the Probe are ribonucleotides.

The present invention provides a Complex in which the Substrate Hybridization Domain is at the 3' end of the Template Nucleic Acid.

The present invention provides a Complex in which the Substrate Hybridization Domain of the Template Nucleic Acid comprises a sequence of about 5 to about 10 nucleotides.

The present invention provides a Complex in which the Substrate Hybridization Domain of the Template Nucleic Acid cannot be extended by a 5'-3' DNA polymerase.

The present invention provides a Complex in which the Substrate Hybridization Domain of the Template Nucleic Acid further comprises an extension of nucleotides at the 3' end of said Substrate Hybridization Domain, the extension having no complementarity to the Template Hybridization Domain of the Substrate Nucleic Acid. the Substrate Hybridization Domain comprises a 3'-terminal modified nucleotide. The modification is selected from the group consisting of: a 3'-amino-modifier, a 2',3'-dideoxynucleotide, a 3'-phosphate, and a modified 3'-phosphate group.

The present invention provides a Complex in which the Substrate Hybridization Domain comprises at least one nucleotide which comprises a modified cytidine, which nucleotide is selected from the group consisting of: C5-methyl-dC and C5-propynyl-dC.

The present invention further provides a Complex in which the Signal Domain of the Probe comprises a sequence of about 10 to about 50 nucleotides.

The present invention further provides a Complex in which the Signal Domain is at least 50%, at least 70%, at least 90% or 100% homopolymeric.

The present invention further provides a Complex in which the at least 60%, at least 80% or 100% of the nucleotides of the Template Hybridization Domain comprise guanosine or cytidine or a combination thereof.

The present invention yet further provides a Complex in which the at least 60% of the nucleotides of the Template Hybridization Domain comprise guanosine or cytidine or a combination thereof, and the Signal Domain is at least 50% homopolymeric.

The present invention further provides a reaction mixture for use in a process for the labeling of a nucleic acid molecule comprising a Template Nucleic Acid comprising, from 3' to 5', a Substrate Hybridization Domain and a Signal Template Domain, wherein the Substrate Hybridization Domain comprises a sequence of about 5 to about 20 nucleotides, and the Signal Template Domain comprises a sequence of about 5 to about 100 nucleotides; and a Substrate Nucleic Acid comprising from 3' to 5', a Template Hybridization Domain and a Target Binding Domain, wherein the Template Hybridization Domain comprises a sequence of about 5 to about 20 nucleotides, is detectably labeled, and shows complementarity toward and is hybridizable to the Substrate Hybridization Domain of the Template Nucleic Acid; the Target Binding Domain is not detectably labeled and comprises a nucleotide sequence heterologous to that of the Template Hybridization Domain of the Substrate Nucleic Acid.

The present invention further provides a kit for labeling a nucleic acid molecule, comprising a reaction mixture comprising Template Nucleic Acid comprising, from 3' to 5', a Substrate Hybridization Domain and a Signal Template Domain, wherein the Substrate Hybridization Domain comprises a sequence of about 5 to about 20 nucleotides, and the Signal Template Domain comprises a sequence of about 5 to about 100 nucleotides; a Substrate Nucleic Acid comprising from 3' to 5', a Template Hybridization Domain and a Target Binding Domain, wherein the Template Hybridization Domain comprises a sequence of about 5 to about 20 nucleotides, is not detectably labeled, and shows complementarity toward and is hybridizable to the Substrate Hybridization Domain of the Template Nucleic Acid; the Target Binding Domain is not detectably labeled and comprises a nucleotide sequence heterologous to that of the Template Hybridization Domain of the Substrate Nucleic Acid; and a DNA polymerase.

The Probes of the invention can be used as either single stranded probes or, when complexed to Template Nucleic Acids, as partially double stranded nucleic acid probes. The double stranded region of such a probe will not interfere with specific binding of the unique sequence at the 5' end of the molecule. The Probes can be used in a variety of assays, including but not limited to electrophoretic mobility shift assays, protein binding assays, Southern blots, Northern blots, Southwestern blots, dot blots, slot blots, colony and plaque lifts, and in situ hybridizations.

3.1 Definitions

Oligonucleotide: An oligonucleotide is single stranded nucleic acid molecule that is relatively short, generally no longer than about 150 nucleotides. An oligonucleotide can be a deoxyribonucleic acid, a ribonucleic acid, or a hybrid thereof.

Template Nucleic Acid: A Template Nucleic Acid is preferably an oligonucleotide, and comprises, from 3' to 5', a domain referred to herein as a "Substrate Hybridization Domain" or "Substrate Binding Domain" and a domain referred to herein as a "Signal Template Domain." The Substrate Hybridization Domain hybridizes to the Template Hybridization Domain of the Substrate Nucleic Acid, and is preferably at the 3'-terminus of the molecule. Upon hybridization of the Substrate Hybridization domain is the "Signal Template Domain", which upon hybridization of the Substrate Hybridization Domain to the Substrate Nucleic Acid, the Signal Template Domain forms a single stranded 5' overhang in a heteroduplex that can be used to extend the Substrate Nucleic Acid strand using a DNA polymerase and labeled nucleotides. The Template Nucleic Acid has a sequence independent from and heterologous to the sequence of the Target Binding Domain of the Substrate Nucleic Acid (see below), and can, therefore, be used for labeling any Substrate Nucleic Acid of interest. As such, this sequence is a "universal" sequence, and, therefore, can also be referred to as a "Universal Template Nucleic Acid."

Substrate Nucleic Acid: A nucleic acid, preferably an oligonucleotide, comprising from 3' to 5', a domain herein referred to as a "Template Hybridization Domain" or "Template Binding Domain" that is complementary to the Substrate Hybridization Domain of the Template Nucleic Acid and is heterologous to, i.e., does not follow the Target Binding Domain in its native context, for example in the gene to which the Target Binding Domain corresponds; and a domain referred to herein as a "Target Binding Domain", which is a specific sequence for binding to a Target molecule of choice, e.g. for detection of a Target Nucleic Acid sequence or to test binding of a Target Protein to a particular DNA or RNA sequence in an electrophoretic mobility shift assay. After hybridization of the Substrate Nucleic Acid to the Template Nucleic Acid, the Template Hybridization Domain can serve as a primer for the extension of the Substrate Nucleic Acid via a DNA polymerase in the presence of at least one labeled nucleotide, with the Signal Template Domain of the Template Nucleic Acid functioning as a template for the extension reaction. The 3' domain of the Substrate Nucleic Acid and the molecule as a whole resulting from the extension are the "Signal Domain" and the "Probe," respectively.

Complex: As used herein, a "Complex" comprises a fully or partially hybridized pair of nucleic acids, for example a Template Nucleic Acid and a Substrate Nucleic Acid, wherein the Substrate Nucleic Acid is labeled. The Substrate Nucleic Acid in such a complex optionally comprises a complete or partial Signal Domain. The term "a Complex comprising partially hybridized pair of nucleic acids" indicates that the nucleic acids of the complex are hybridized to each other over least five contiguous nucleotides.

Homopolymeric: A homopolymeric nucleic acid or nucleic acid domain is a nucleic acid or nucleic acid domain in which the base composition of each of the nucleotides is the same, e.g., poly-A. When a nucleic acid or nucleic acid sequence is said to be x % homopolymeric, then the base composition of x % of the nucleotides of the nucleic acid is the same. Such nucleotides can be but are not necessarily contiguous.

Target: As used herein, and unless indicated otherwise, the term "Target" refers to a molecule to which a Probe produced by the methods of the invention is designed to bind. The Target can be any molecule to which a Probe can bind. The Target can be a nucleic acid (a Target Nucleic Acid). For example, the Probe can be utilized for detection of the Target Nucleic Acid in a sample via hybridization to the Probe. The Target can also, for example, be a protein (a Target Protein). The Probe can be utilized, for example, in an electrophoretic mobility shift assay to detect a Target Protein that binds the Probe.

Probe: As used herein, the term "Probe" refers to the labeled nucleic acid generated by extension of the Substrate Nucleic Acid according to the methods of the present invention. The term is also meant to encompass a Complex comprising a labeled (i.e., Probe) nucleic acid strand.

Binding domain: As used herein, a Binding Domain is a region of complementarity between the Substrate Nucleic Acid and the Template Nucleic Acid. The Binding Domain of the Substrate Nucleic Acid is the Template Binding Domain and the Binding Domain of the Template Nucleic Acid is the Substrate Binding Domain. A Binding Domain can be utilized as part of any Template or Substrate Nucleic Acid molecule, and, therefore, can be considered a "universal" sequence. As such, this term can also be referred to as a "Universal Binding Domain." The term "Template Binding Domain" is used interchangeably with the term "Template Hybridization Domain", and the term "Substrate Binding Domain" is used interchangeably with the term "Substrate Hybridization Domain."

Adenosine/cytidine/guanosine/thymidine/uridine: As used herein, adenosine, cytidine, guanosine thymidine and uridine refer to both the ribonucleosides and the deoxyribonucleosides, unless otherwise indicated.

Hybridization: The term "hybridizable to", when referring to the association between the Substrate and Template Nucleic Acids, indicates hybridization under conditions of moderate to high stringency. Conditions of moderate to high stringency which may be used depend on the nature of the nucleic acid (e.g. length, GC content, etc.) and are well known in the art. For example, stringent hybridization of a Template Nucleic Acid to a Substrate Nucleic Acid over a region of approximately 15 bases is done under the following conditions: a salt concentration of 50 mM KCl, a buffer concentration of 10 mM Tris-HCl, a $Mg^{2+}$ concentration of 1.5 mM, a pH of 7–7.5 and an annealing temperature of 55–60° C. Selection of other appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, 1987-present, Current Protocols, John Wiley and Sons, Inc.).

Complementary/Complementarity: These terms, as used herein, refer to a degree of base-pairing complementarity between two nucleic acid sequences that allows hybridization under the conditions described above. In a preferred embodiment, the degree of complementarity between two nucleic acids is 100%.

4. BRIEF DESCRIPTION OF THE FIGURES

FIGS. 1A–D: A schematic representation of a preferred embodiment of the present invention. (A(i)) The design of the Substrate Nucleic Acid where the Ns can be any nucleotide and represent the Target Binding Domain of the Substrate Nucleic Acid and the hatched box represents the Universal Template Hybridization Domain. (A(ii)) The Template Nucleic Acid, where the hatched box represents a sequence complementary to the Template Hybridization Domain in (1A) (the Substrate Hybridization Domain) and the 5' oligo-dT represents the Signal Template Domain. (B) Annealing of the Substrate and Template Nucleic Acids at their respective binding sites. (C) Labeling of the Substrate by primer extension on the oligo-dT Template in the presence of buffer, $\alpha$-$^{32}$P-dATP, and DNA polymerase. (D) Removal of unincorporated $\alpha$-$^{32}$P-dATP by column chromatography and, optionally, removal of the Template Nucleic Acid and any unlabeled products by preparative PAGE to yield a highly Probe with a specific activity many fold higher than when labeled by conventional methods.

FIGS. 2A–B: Evaluation of primer extension reaction products. (A) Substrate and Template Nucleic Acid Strands. Template Nucleic Acids in which Substrate Hybridization Domains were of 4, 5, or 6 nucleotides in length were compared for efficiency in promoting primer extension of the Substrate Nucleic Acid. The nucleotides of the binding domain within the Template Nucleic Acid strand were modified to include deoxycytidine (dC), C5—methyl-dC, (5-me-dC) or C5-propynyl-dC as indicated. In this study, the Substrate Nucleic Acid was initially labeled at the 5' end with $^{32}PO_4$ by PNK and then extended with unlabeled dATP in order to define relative reaction efficiencies of Template Nucleic Acids which varied in the length and chemical composition of their Substrate Hybridization Domains. (B) PAGE analysis of reaction products. Reaction products were separated by analytical PAGE and visualized by phosphorimaging.

FIG. 3: The percent of the total Substrate Nucleic Acid that is extended in the primer extension (labeling) reaction. Bands from the image shown in FIG. 2 were quantitatively measured using phosphorimaging and a graphical depiction is shown as the percent ratio of Substrate Nucleic Acid extended to total Substrate Nucleic Acid in the reaction mixture.

Figure 4B:
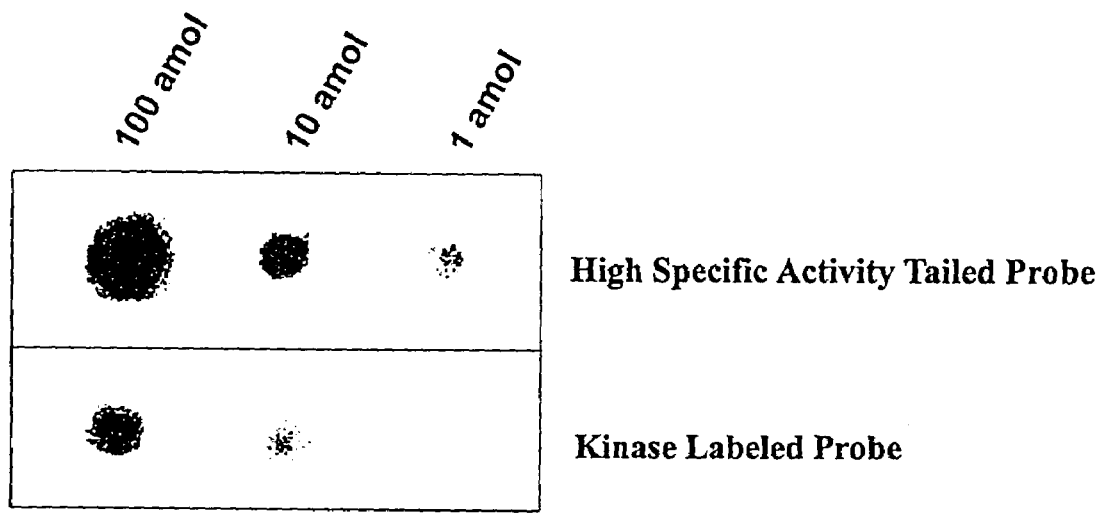

FIGS. 4A–B: Dot blot assay comparing the detection efficiency (sensitivity) of a Target Nucleic Acid by a Probe labeled by the methods of the present invention compared to a probe labeled with T4 PNK. A) Probes: A Substrate oligonucleotide with a Target Binding Domain complementary to the plasmid target (pGreen Lantern™-1, Life Technologies, Inc.) was labeled using the methods described herein or by T4 PNK. The base composition and radioactive $^{32}$P label content of both probes are shown. B) Dot Blot Assay: A decreasing mass-titration of the plasmid target was spotted onto two nylon membranes in amounts as indicated. An equal amount of radioactivity per probe (as measured by counts per minute (CPM)), was hybridized to the blots. Both blots were pre-hybridized, hybridized, and washed in an identical fashion as described in Example 2. Results were visualized using a Packard Cyclone Phosphor Imaging system.

Figure 5B:
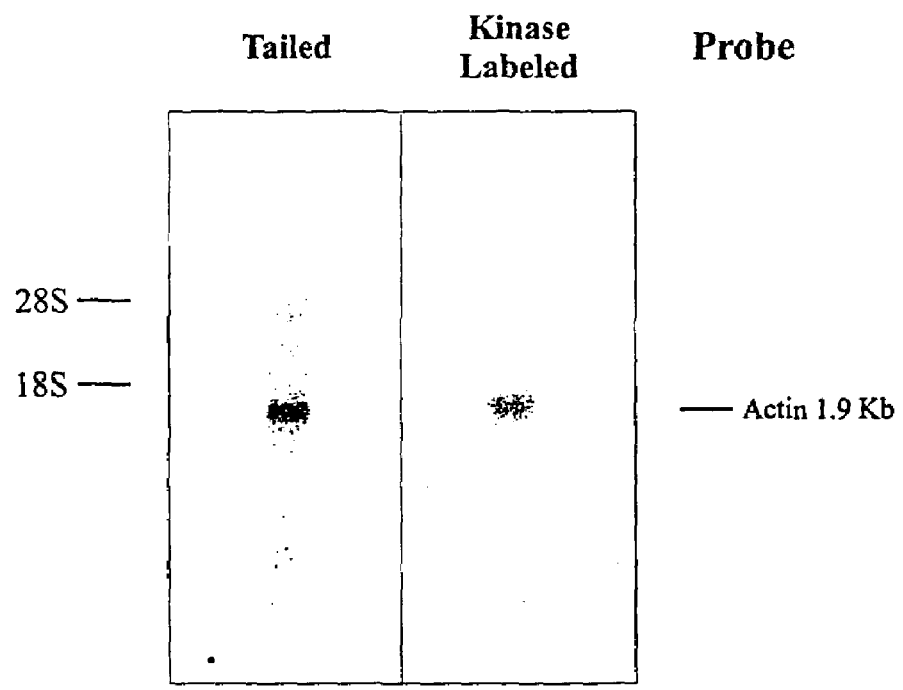

FIGS. 5A–B: Northern blot of human placental RNA comparing the detection efficiency (sensitivity) of a Target Nucleic Acid by a Probe labeled by the methods of the present invention with T4 PNK. (A) Probes: A Substrate oligonucleotide with a Target Binding Domain complementary to human β-actin was labeled using the methods described herein or using T4 PNK. The base composition and radioactive $^{32}$P label content of both probes are shown. (B) Northern Blot: Ten micrograms of human placental total RNA was separated on each lane of a formaldehyde agarose gel and transferred to nylon membranes. An equal amount radioactivity per probe (as measured by counts per minute (CPM)) was hybridized to the blots. Both blots were prehybridized, hybridized, and washed in an identical fashion as described in Example 3. Results were visualized using a Packard Cyclone Phosphor Imaging system. Position of 18S and 28S ribosomal RNA bands are indicated as size markers.

Figure 6B:
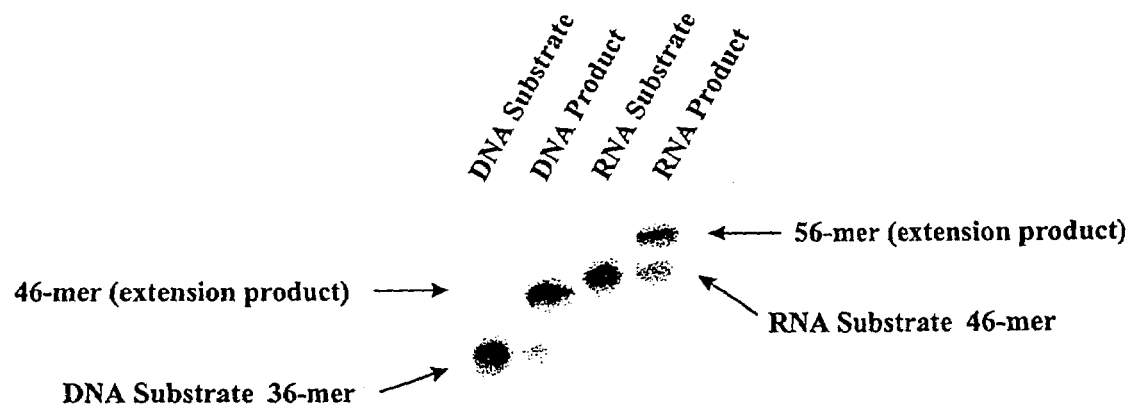

FIGS. 6A–B: Primer extension reaction using an RNA Substrate Nucleic Acid. (A) Substrate Nucleic Acids and Reaction Products. DNA and RNA Substrate Nucleic Acid molecules were initially labeled at the 5' end with $^{32}$PO$_4$ by PNK and then extended with unlabeled dATP in order to define an RNA substrate composition. (B) PAGE analysis of reaction products. Reaction products were separated by analytical PAGE and visualized by phosphorimaging. Position of Substrate and Probe bands are indicated.

5. DETAILED DESCRIPTION OF THE INVENTION

The present invention is directed to methods for the generation of nucleic acid probes. The invention is also directed to nucleic acid probes generated by the methods of the invention, reaction mixtures for producing the probes, and kits comprising reagents for the generation of such probes.

The present invention provides a method of labeling a nucleic acid molecule, comprising the steps of hybridizing a first nucleic acid, the Template Nucleic Acid, to a second nucleic acid, the Substrate Nucleic Acid. The Template Nucleic Acid comprises, from 3' to 5', a Substrate Hybridization Domain and a Signal Template Domain, wherein the Substrate Hybridization Domain comprises a sequence of about 5 to about 20 nucleotides and the Signal Template Domain comprises a sequence of about 5 to about 100 nucleotides. The Substrate Nucleic Acid comprises, from 3' to 5', a Template Hybridization Domain and a Target binding domain, wherein the Template Hybridization Domain comprises a sequence of about 5 to about 20 nucleotides, is not detectably labeled, and shows complementarity toward and is hybridizable to the Substrate Hybridization Domain of the Template Nucleic Acid, and the Target Binding Domain is not detectably labeled and comprises a nucleotide sequence heterologous to that of the Template Hybridization Domain of the Substrate Nucleic Acid. After the Template Nucleic Acid is hybridized to the Substrate Nucleic Acid, the Substrate Nucleic Acid is extended in the presence of at least one labeled nucleotide triphosphate to create a Signal Domain having a sequence which shows complementarity toward and is hybridizable to the Signal Template Domain of the Template Nucleic Acid. The resulting Probe can be purified from any remaining nucleic acid for example by PAGE, to obtain a known species of high specific activity. Similarly, the Probe can be isolated from the Complex (i.e., the Probe-Template Nucleic Acid Complex) produced by the extension reaction, e.g., via denaturation (for example by heat or alkali) followed by such Probe strand purification.

The present invention further provides a Probe comprising, from 3' to 5', a Signal Domain, a Template Hybridization Domain and a Target Binding Domain, wherein the Signal Domain comprises a sequence of about 5 to about 100 nucleotides of which at least two nucleotides are detectably labeled; the Template Hybridization Domain comprises a sequence of about 5 to about 20 nucleotides, and is not detectably labeled; and the Target Binding Domain is not detectably labeled and comprises a nucleotide sequence heterologous to that of the Template Hybridization Domain.

In one embodiment, the nucleotides which comprise the Probe are deoxyribonucleotides. In another embodiment, the nucleotides which comprise the Signal Domain of the Probe are deoxyribonucleotides and the nucleotides which comprise the Template Hybridization Domain and the Target Binding Domain of the Probe are ribonucleotides. In certain embodiments of the invention, the Signal Domain of the Probe comprises a sequence of about 10 to about 50 nucleotides.

The Signal Domain of the invention comprises at least two labeled nucleotides. In certain embodiments, the Signal Domain comprises at least three labeled nucleotides, more preferably at least four labeled nucleotides, more preferably at least five labeled nucleotides, and yet more preferably about 10 labeled nucleotides. In other embodiments, the Signal Domain comprises fewer than 20 labeled nucleotides. In yet other embodiments, all the nucleotides which comprise the Signal Domain of the invention are labeled.

The present invention provides a Probe in which the Signal Domain is at least 50%, at least 70%, at least 90% or 100% homopolymeric.

The present invention provides a Probe in which at least one nucleotide comprises a label selected from the group consisting of: $^{32}$P, $^{33}$P, $^{35}$S, fluorescein, digoxigenin, biotin, Cy5, Cy3, and rhodamine.

The present invention provides a Probe in which the Template Hybridization Domain comprises a sequence of about 5 to about 10 nucleotides.

The present invention further provides a Probe in which at least 60%, at least 80% or 100% of the nucleotides of the Template Hybridization Domain comprise guanosine or cytidine or a combination thereof. In instances wherein 100% of the nucleotides of the Template Hybridization Domain comprise guanosine or cytidine, it is preferred that there be a combination of guanosine and cytidine present.

In certain embodiments of the present invention, at least 60% of the nucleotides of the Template Hybridization Domain of the Probe comprise guanosine or cytidine or a combination thereof, and the Signal Domain of the Probe is at least 50% homopolymeric.

The present invention further provides a Complex, comprising a Template Nucleic Acid comprising, from 3' to 5' a Substrate Hybridization Domain and a Signal Template Domain, wherein the Substrate Hybridization Domain comprises a sequence of about 5 to about 20 nucleotides and the Signal Template Domain comprises a sequence of about 5 to about 100 nucleotides; and a Probe comprising from 3' to 5' a Signal Domain, a Template Hybridization Domain and a Target Binding Domain, wherein the Signal Domain comprises a sequence of about 5 to about 100 nucleotides, which sequence shows complementarity toward and is hybridizable to the Signal Template Domain of the Template Nucleic Acid, and of which at least two nucleotides are detectably labeled; the Template Hybridization Domain comprises a sequence of about 5 to about 20 nucleotides, is not detectably labeled, and shows complementarity toward and is hybridizable to the Substrate Hybridization Domain of the Template Nucleic Acid; the Target Binding Domain is not detectably labeled and comprises a nucleotide sequence heterologous to that of the Template Hybridization Domain of the Substrate Nucleic Acid.

The present invention provides a Complex in which the nucleotides which comprise the Probe or Template Nucleic Acid are deoxyribonucleotides. The present invention provides a Complex in which the nucleotides which comprise Template Nucleic Acid are ribonucleotides. The present invention provides a Complex in which the nucleotides which comprise the Signal Domain of the Probe are deoxyribonucleotides and the nucleotides which comprise the Template Hybridization Domain and the Target Binding Domain of the Probe are ribonucleotides.

The present invention provides a Complex in which the Substrate Hybridization Domain is at the 3' end of the Template Nucleic Acid.

The present invention provides a Complex in which the Substrate Hybridization Domain of the Template Nucleic Acid comprises a sequence of about 5 to about 10 nucleotides.

The present invention provides a Complex in which the Substrate Hybridization Domain of the Template Nucleic Acid cannot be extended by a 5'→3' DNA polymerase.

The present invention provides a Complex in which the Substrate Hybridization Domain of the Template Nucleic Acid further comprises an extension of nucleotides at the 3' end of said Substrate Hybridization Domain, the extension having no complementarity to the Template Hybridization Domain of the Substrate Nucleic Acid. the Substrate Hybridization Domain comprises a 3'-terminal modified nucleotide. The modification is selected from the group consisting of: a 3'-amino-modifier, a 2',3'-dideoxynucleotide, a 3'-phosphate, and a modified 3'-phosphate group.

The present invention provides a Complex in which the Substrate Hybridization Domain comprises at least one nucleotide which comprises a modified cytidine, which nucleotide is selected from the group consisting of: C5-methyl-dC and C5-propynyl-dC.

The present invention further provides a Complex in which the Signal Domain of the Probe comprises a sequence of about 10 to about 50 nucleotides.

The present invention further provides a Complex in which the Signal Domain is at least 50%, at least 70%, at least 90% or 100% homopolymeric.

The present invention further provides a Complex in which the at least 60%, at least 80% or 100% of the nucleotides of the Template Hybridization Domain comprise guanosine or cytidine or a combination thereof. In instances wherein 100% of the nucleotides of the Template Hybridization Domain comprise guanosine or cytidine, it is preferred that there be a combination of guanosine and cytidine present.

The present invention yet further provides a Complex in which the at least 60% of the nucleotides of the Template Hybridization Domain comprise guanosine or cytidine or a combination thereof, and the Signal Domain is at least 50% homopolymeric.

The present invention further provides a reaction mixture for use in a process for the labeling of a nucleic acid molecule comprising a Template Nucleic Acid comprising, from 3' to 5', a Substrate Hybridization Domain and a Signal Template Domain, wherein the Substrate Hybridization Domain comprises a sequence of about 5 to about 20 nucleotides, and the Signal Template Domain comprises a sequence of about 5 to about 100 nucleotides; and a Substrate Nucleic Acid comprising from 3' to 5', a Template Hybridization Domain and a Target Binding Domain, wherein the Template Hybridization Domain comprises a sequence of about 5 to about 20 nucleotides, is not detectably labeled, and shows complementarity toward and is hybridizable to the Substrate Hybridization Domain of the Template Nucleic Acid; the Target Binding Domain is not detectably labeled and comprises a nucleotide sequence heterologous to that of the Template Hybridization Domain of the Substrate Nucleic Acid.

The present invention further provides a method for detecting a Target Nucleic Acid in a sample, comprising contacting the sample with a Probe (comprising a Substrate Nucleic Acid comprising a Signal Domain, which is optionally hybridized or cross linked to a Template Nucleic Acid) under conditions whereby said Probe can bind to the Target Nucleic Acid to form a Probe-Target hybrid; and detecting any Probe-Target Nucleic Acid hybrids, so that if a Probe-Target Nucleic Acid hybrid is detected, a Target Nucleic Acid is detected in the sample.

The present invention further provides a kit for labeling a nucleic acid molecule, comprising a reaction mixture comprising Template Nucleic Acid comprising, from 3' to 5', a Substrate Hybridization Domain and a Signal Template Domain, wherein the Substrate Hybridization Domain comprises a sequence of about 5 to about 20 nucleotides, and the Signal Template Domain comprises a sequence of about 5 to about 100 nucleotides; a Substrate Nucleic Acid comprising from 3' to 5', a Template Hybridization Domain and a Target Binding Domain, wherein the Template Hybridization Domain comprises a sequence of about 5 to about 20 nucleotides, is not detectably labeled, and shows complementarity toward and is hybridizable to the Substrate Hybridization Domain of the Template Nucleic Acid; the Target Binding Domain is not detectably labeled and comprises a nucleotide sequence heterologous to that of the Template Hybridization Domain of the Substrate Nucleic Acid; and a DNA polymerase.

5.1 Substrate Nucleic Acid and Template Nucleic Acid Sequences

The present invention provides a Template Nucleic Acid comprising, from 3' to 5', a Substrate Hybridization Domain and a Signal Template Domain, wherein the Substrate Hybridization Domain comprises a sequence of about 5 to about 20 nucleotides and the Signal Template Domain comprises a sequence of about 5 to about 100 nucleotides. The present invention also provides a Substrate Nucleic Acid comprising, from 3' to 5,' a Template Hybridization Domain and a Target Binding Domain, wherein the Template Hybridization Domain comprises a sequence of about 5 to about 20 nucleotides, is not detectably labeled, and shows complementarity toward and is hybridizable to the Substrate Hybridization Domain of the Template Nucleic Acid, and the Target Binding Domain is not detectably labeled and comprises a nucleotide sequence heterologous to that of the Template Hybridization Domain of the Substrate Nucleic Acid.

The Substrate and Template Nucleic Acids of the invention can comprise ribonucleotides or deoxyribonucleotides, or a combination thereof. The Probes of the invention can comprise deoxyribonucleotides or a combination of deoxyribonucleotides and ribonucleotides, wherein the nucleotides which comprise the Signal Domain are deoxyribonucleotides. In one embodiment, the nucleotides which comprise the Signal Domain of a Probe are deoxyribonucleotides and the nucleotides which comprise the Template Hybridization Domain and the Target Binding Domain of the same Probe are ribonucleotides.

The Substrate Nucleic Acid of the invention can be from about 15 to about 10,000 nucleotides. In certain embodiments, the Substrate Nucleic Acid is about 15 to about 150 nucleotides. In other embodiments, the Substrate Nucleic Acid is about 50 to about 10,000 nucleotides. Preferably, the Substrate Nucleic Acid is about 15 to about 500 nucleotides, more preferably about 20 to about 300 nucleotides, more preferably from about 25 to about 200 nucleotides, and most preferably from about 30 to about 100 nucleotides.

The Target Binding Domain of the invention can be from about 10 to about 10,000 nucleotides. In certain embodiments, the Target Binding Domain is about 10 to about 150 nucleotides. In other embodiments, the Target Binding Domain is about 50 to about 10,000 nucleotides. Preferably, the Target Binding Domain is about 10 to about 500 nucleotides, more preferably about 15 to about 300 nucleotides, more preferably from about 20 to about 200 nucleotides, and most preferably from about 25 to about 100 nucleotides.

5.1.1 Template and Substrate Hybridization Domains

The Substrate Hybridization and Template Hybridization Domain sequences are preferably short so as not to interfere with the use of the Template Nucleic Acid/Probe Complex as hybridization probe. A Substrate or Template Hybridization Domain of about 5 to about 20 bases in length is preferred, with a length of about 5 to about 10 bases in length being most preferred. Sequences shorter than 5 bases can be used but generally give lower yields of the labeled extension product (FIG. 2 and FIG. 3). Sequences longer than bases can also be used, but are preferably no longer than approximately 20 nucleotides.

Preferably, at least 60%, more preferably at least 80%, and most preferably 100% of the nucleotides of the Template Hybridization Domain comprise guanosine or cytidine or a combination thereof. In instances wherein 100% of the nucleotides of the Template Hybridization Domain comprise guanosine or cytidine, it is preferred that there be a combination of guanosine and cytidine present.

In one embodiment of the invention, at least 60% of the nucleotides of the Template Hybridization Domain comprise guanosine or cytidine or a combination thereof, and the Signal Domain is at least 50% homopolymeric.

In a preferred embodiment, the Substrate Hybridization Domain is located at the 3' of the Template Nucleic Acid. In other embodiments, the Substrate Hybridization Domain is located near but not at the 3' of the Template Nucleic Acid. In the latter embodiment a 3' overhang results when the Template Nucleic Acid is hybridized to the Substrate Nucleic Acid. A 3' overhang that is not complementary to the Target Hybridization Domain of the Substrate Nucleic Acid can serve to functionally block the 3' end of the Template Nucleic Acid from primer extension by the polymerase used in the extension reaction.

In certain embodiments of the invention, the Substrate Hybridization Domain cannot be extended by a 5'→3' DNA. In one embodiment, the Substrate Hybridization Domain cannot be extended by a 5'→3' DNA polymerase because it further comprises an extension of nucleotides at the 3' end of the Substrate Hybridization Domain, the extension having no complementarity to the Template Hybridization Domain of the Substrate Nucleic Acid, as discussed above. The 3' extension of the Substrate Hybridization Domain is preferably less than 20 nucleotides, more preferably less than 10 nucleotides, more preferably less than 5 nucleotides, and most preferably 2 or 3 nucleotides. In one embodiment, the Substrate Hybridization Domain cannot be extended by a 5'→3' DNA polymerase because the Substrate Hybridization Domain comprises a 3'-terminal modified nucleotide. In certain modes of the embodiment, the modification is selected from the group consisting of a 3'-amino-modifier, a 2',3'-dideoxynucleotide, a 3'-phosphate, and a modified 3'-phosphate group. A 3' amino modifier is an aliphatic chain comprising a primary amino group, which amino group is covalently linked to the 3' OH group of a nucleic acid.

In a preferred embodiment, the Substrate Hybridization Domain to be used as a Substrate Hybridization Domain is GGCGGG, (SEQ ID NO:1). Such a domain is entirely GC in composition, allowing for high affinity binding to the Template Hybridization Domain, which in turn permits the sequence to be minimal in length. Such a domain can only hybridize to the Template Hybridization Domain in a single alignment, and thus no "slippage" can occur. One hundred percent homopolymeric Template Hybridization Domains (e.g., GGGGGG (SEQ ID NO:2) or CCCCCC (SEQ ID NO:3), therefore, are not preferred. Using the exemplary, non-limiting Substrate and Template Binding Domains (see Section 5.1.3 below), all Template Nucleic Acid—Substrate Nucleic Acid Complexes formed are optimally aligned and can, therefore, optimally participate in the extension reaction. An additional feature of the preferred Substrate Hybridization Domain is that it is guanosine rich, and thus its complement in the Template Nucleic Acid is cytidine rich. This allows for incorporation of dC-heterocyclic base-modifications into the Template Nucleic Acid as opposed to the Substrate Nucleic Acid. Use of costly modified-base reagents, such as C5-propynyl-dC or C5-methyl-dC, is more economical when incorporated into the Template Nucleic Acid rather than the Substrate Nucleic Acid, since, because any Substrate Nucleic Acid can be synthesized to include a 3' Template Hybridization Domain, a single heterologous Template can be used in hundreds or thousands of diffeenct Substrate Nucleic Acids and can be utilized for a wide range of labeling reactions, including labeling reactions that simultaneously or individually generate different Probes.

The 3' end of the Template Nucleic Acid can be blocked to prevent the Substrate Nucleic Acid from acting as a template in an undesired primer extension reaction and thereby labeling the Template Nucleic Acid as well. Function blocking can be achieved by the addition of non-complementary bases at the 3' end as described above. Blocking can also be achieved through chemical modification of the 3' terminal sugar group. Blocking groups which may be used include, but are not limited to, 3'-amino-modifiers, a 2',3'-dideoxynucleotide, a 3'-phosphate or a modified 3'-phosphate group (i.e., —P—O—R, where R is selected from an alkyl group, an alcohol (e.g. $CH_2CH_2CH_2OH$) or a derivative of ethylene glycol, (e.g., $CH_2CH_2$—O—). While a blocking group is not required its use eliminates the potential for undesired side reactions.

In certain preferred embodiments of the invention, the Substrate Hybridization Domain comprises at least one nucleotide which comprises a modified cytidine, which nucleotide is selected from the group consisting of: C5-methyl-dC and C5-propynyl-dC.

5.1.2 Signal Template and Signal Domains

According to the present invention, the Signal Domain of the Probe comprises a sequence of about 5 to about 100 nucleotides, which sequence shows complementarity toward and is hybridizable to the Signal Template Domain of the Template Nucleic Acid, of which at least two nucleotides are detectably labeled. Likewise, the size of the Signal Template Domain is generally from about 5 to about 100 nucleotides.

In a preferred embodiment, the Signal Template or Signal Domain is at least 50% homopolymeric, more preferably at least 70% homopolymeric, more preferably at least 90% homopolymer, and most preferably is a homopolymer (e.g., poly-A). In instances wherein a Probe of the invention is to be utilized for detecting Targets in a sample that contain or are suspected of containing mRNA species, a homopolymeric poly-T or poly-dT Signal Domain is not preferred. An advantage of a homopolymeric Signal Domain is that only one type of nucleotide needs to be used in the extension reaction that generates the probe, for example, $^{32}$P-dATP. In a preferred embodiment, the Signal Template Domain is oligo-dT (or oligo-U).

The Signal Template domain or the Signal Domain is preferably from about 5 to about 100 nucleotides, more preferably from about 5 to about 75 nucleotides, more preferably from about 5 to about 50 nucleotides, and most preferably from about 5 to about nucleotides.

In one embodiment of the invention, the Substrate Nucleic Acid is extended to produce the Signal Domain using a nucleotide triphosphate that comprises a label selected from the group consisting of $^{32}$P, $^{33}$P, $^{35}$S, fluorescein, digoxigenin, biotin, Cy5, Cy3, and rhodamine. In certain modes of the embodiment, the nucleotide triphosphate is selected from the group consisting of α-$^{32}$P-dATP, α-$^{33}$P-dATP, α-$^{35}$S-dATP, fluorescein-15-dATP, digoxigenin-16-dATP, biotin-7-dATP, and biotin-21-dATP.

5.1.3 Exemplary Embodiment

In an exemplary embodiment, presented herein by way of example and not by way of limitation, the Substrate and Template Nucleic Acid Comprise the following sequences (in which N is any ribonucleotide or deoxyribonucleotide):

```
Target Binding Domain of Substrate Nucleic Acid
5'-NNNNNNNNNNNNNNNNNNNNN-3' (SEQ ID NO:4)

Template Hybridization Domain of Substrate Nucleic
Acid:
5'-GGCGGG-3' (SEQ ID NO:1)

Substrate Nucleic Acid:
5'-NNNNNNNNNNNNNNNNNNNNNGGCGGG3' (SEQ ID NO:5)

Signal Template Domain of Template Nucleic Acid:
5'-TTTTTTTTTT-3' (SEQ ID NO:6)

Substrate Hybridization Domain of Template Nucleic
Acid:
5'-CCCGCC-C₇-amino-modifier-3' (SEQ ID NO:7)

Template Nucleic Acid:
5'-TTTTTTTTTTCCCGCC-C₇-amino-modifier-3'
(SEQ ID NO:8)
```

In a preferred embodiment the Template Nucleic Acid is modified to improve labeling efficiency. In a preferred mode of the embodiment, the modification is the substitution of the dC nucleotide of the Substrate Binding Domain with 5-methyl-deoxycytidine (mC), or even more preferably, with C5-propynyl-dC (pC). In the exemplary embodiment above, modification of the Template Nucleic Acid with mC orpPC would result in:

```
Template Nucleic Acid with methyl-dC modifier:
5'-TTTTTTTTTTmCmCmCGmCmC-C₇-amino-mod-3'
(SEQ ID NO:9)

Template Nucleic Acid (propynyl-dC modifier):
5'-TTTTTTTTTTpCpCpCGpCpC-C₇-amino-mod-3'
(SEQ ID NO:10)
```

These heterocyclic base modifications increase the binding affinity of the Substrate Hybridization Domain for the Template Hybridization Domain, allowing for more complete hybridization and therefore a more efficient labeling reaction. Other heterocyclic modifications can be used, e.g. C5-propynyl-dU (as a dT or U substitute), or 2,6-diaminopurine (as a dA or A substitute). Such modifications serve to increase the relative reaction efficiency but are not required for practice of the invention (FIG. 2 and FIG. 3).

The labeling reaction utilizes the synthesis of RNA or DNA to form a covalent attachment between a labeled nucleotide and a substrate nucleic acid by primer extension. The Substrate and Template Nucleic Acids associate with each other, generally through standard Watson-Crick base pairing of 5 or more-base complementary hybridization sequences. In certain embodiments, the Substrate and Template Nucleic Acids associate by non-Watson-Crick hybridization (such as the incorporation of protein nucleic acid residues in the Template Nucleic Acid).

5.2 Nucleic Acid Synthesis

The nucleic acids of the invention may be synthetic oligonucleotides comprised of deoxyribonucleotides, ribonucleotides, combinations (chimeras), or derivatives thereof. The use of ribonucleotide derivatives has been reported by Shibahara et al., Nucleic Acids Research 1989, 17, 239–252. A person skilled in the art is capable of synthesizing oligonucleotides. See for example, Gait, M. J., ed. (1984) Oligonucleotide Synthesis (IRL, Oxford).

In one preferred embodiment, nucleic acid synthesis is performed using solid phase phosphoramidite monomer chemistry with automated synthesizers. Currently nucleic acid strands up to about 150 nucleotides in length can be synthesized chemically using the phosphoramidite method. In other embodiments, other methods of nucleic acid synthesis are used, such as H-phosphonate chemistry. Chemical synthesis of nucleic acids allows for the production of various forms of the nucleic acids with modified linkages and nonstandard bases attached in chosen places throughout the nucleic acid's entire length (Current Protocols in Molecular Biology, John Wiley & Sons, Inc., incorporated herein by reference).

In certain embodiments, the Substrate and Template Nucleic Acids are not chemically but enzymatically synthesized, for example by a DNA or RNA polymerase. Such Substrate Nucleic Acids may be single or double stranded. In certain modes of this embodiment, the Substrate Nucleic Acid is from about 50 nucleotides to about 10,000 nucleotides, more preferably from about 50 to about 1,000 nucleotides, and most preferably from about 50 to about 200 nucleotides. In a preferred mode of this embodiment, the Substrate Nucleic Acid is generated by polymerase chain reaction (PCR), using standard techniques. The Template Hybridization Domain can be added, for example, by ligation or by incorporating the Template Hybridization Domain sequence into the PCR Primers. If the Substrate Nucleic Acid is a PCR product, it is heated to denature it from its complementary strand to allow it to anneal with the Template Nucleic Acid.

When the Substrate Nucleic Acid or Template Nucleic Acid is a ribonucleic acid, it can be generated in a transcriptional reaction. A synthetic or PCR amplified DNA clone encoding the sequence of a Substrate Nucleic Acid or the Template Nucleic Acid is prepared, said DNA having an initiation site for an RNA polymerase. RNA polymerase initiation sites are well known to those of skill in the art (see e.g. Chamberlin and Ryan, 1982, Bacteriophage DNA-dependent RNA polymerases. In The Enzymes, Vol. 15B (P.

D. Boyer, ed.), pp. 87–109. Academic Press, San Diego. Production of the RNA from the synthetic clone by transcription with the appropriate RNA polymerase (e.g. SP6 or T7 RNA polymerase) is achieved using routine approaches which are well known in the art. Suitable RNA polymerases include but are not limited to T3, T7, SP6, BA14, or K11 RNA polymerase. Since RNA polymerases generate heterogenous 3' ends, it is preferred that the Substrate Nucleic Acid or Template Nucleic Acid generated by an RNA polymerase is initially synthesized as longer precursor, then cleaved by a ribozyme or other appropriate enzyme.

The Substrate and Template Nucleic Acids may also be modified at any position with substituents generally known in the art, with the exception of 2' O-modifications of ribonucleic acids.

In one embodiment, the Substrate and Template Nucleic Acids have one or more modifications of the nucleotides which increase bioavailability by enhancing stability to nuclease attack and/or increasing cellular uptake. For example, the modification of the nucleotide backbone bonds from phosphodiesters to phosphorothioates confers greater stability against nuclease attack. Phosphorothioates, i.e., the substitution of a sulfur atom for a phosphate oxygen in the internucloetide phosphodiester linkage, are stable to nuclease cleavage and soluble in lipid. Lipid solubility can be important for bioavailability. Preferably, only the 5' terminal bond of the Substrate and both terminal bonds of the Template Nucleic Acids are modified. In this manner, stability is increased without foresaking cellular uptake. The oligonucleotides can also be protected from exonuclease attack through the addition of amino groups at the ends.

Other modified Substrate and Template Nucleic Acids within the scope of the invention include α-anomeric oligonucleotides. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641).

Additionally, the Substrate and Template Nucleic Acids may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The Substrate and Template Nucleic Acids can also comprise at least one modified sugar moiety selected from the group including but not limited to arabinose, 2-fluoroarabinose, xylulose, and hexose.

The Template Hybridization Domain, which acts as a binding site for the Template Nucleic Acid, is preferably added to a nucleic acid at the time the nucleic acid is prepared, for example during chemical synthesis. In other embodiments, the Template Hybridization Domain is added by fill-in reactions, ligation or PCR.

5.3 Probe Labeling and Purification

Specifically, the invention provides a method of labeling a nucleic acid molecule, comprising the steps of hybridizing a first nucleic acid, the Template Nucleic Acid, to a second nucleic acid, the Substrate Nucleic Acid. The Template Nucleic Acid comprises, from 3' to 5', a Substrate Hybridization Domain and a Signal Template Domain, wherein the Substrate Hybridization Domain comprises a sequence of about 5 to about 20 nucleotides and the Signal Template Domain comprises a sequence of about 5 to about 100 nucleotides. The Substrate Nucleic Acid comprises, from 3' to 5', a Template Hybridization Domain and a Target binding domain, wherein the Template Hybridization Domain comprises a sequence of about 5 to about 20 nucleotides, is not detectably labeled, and shows complementarity toward and is hybridizable to the Substrate Hybridization Domain of the Template Nucleic Acid, and the Target Binding Domain is not detectably labeled and comprises a nucleotide sequence heterologous to that of the Template Hybridization Domain of the Substrate Nucleic Acid. Upon hybridization, the Substrate Nucleic Acid is extended with a DNA polymerase in the presence of a labeled nucleotide to create a Signal Domain having a sequence which shows complementarity toward and is hybridizable to the Signal Template Domain of the Template Nucleic Acid.

The first step of the labeling methods of the present invention, after synthesis of the Substrate and Template Nucleic Acids, is hybridizing the two strands via the Template and Substrate Hybridization Domains, respectively. Hybridizing does not require special conditions and can be done simply by mixing the two nucleic acids together under standard conditions well known to those of skill in the art, e.g., in a low salt, buffered aqueous solution; heat denaturation and cooling may facilitate hybridization. In certain embodiments, hybridization is preceded by heat denaturation and cooling of the nucleic. In a preferred embodiment the Template Nucleic Acid present in the reaction mixture is in excess over the Substrate Nucleic Acid, preferably a 5 to 50-fold molar excess, most preferably a 5 to 25-fold molar excess. Lower molar ratios will still result in labeling, albeit at lower efficiencies. Increasing Template Nucleic Acid above 50-fold molar excess over the Substrate Nucleic Acid does not improve reaction efficiency.

Preferably, the heating step is done in a water bath or other heating device at 94° C. for one minute, although different temperatures and incubation times will also suffice, as can be determined by one of skill in the art. An extended annealing or hybridization step at controlled temperature is not necessary. The reaction buffer is preferably 10 mM Tris pH 7.5, 5 mM $MgCl_2$, and 7.5 mM dithiothreitol (DTT). However, other buffers may be utilized, depending on the DNA polymerase of choice and as reaction conditions permit. Appropriate conditions for the DNA polymerase of choice are well known to those of skill in the art. The nucleic acid mixture is transferred from the heat source and allowed to cool to room temperature under ambient conditions.

The Substrate Nucleic Acid is then extended with a DNA polymerase in the presence of a labeled nucleotide(see Section 5.5, below) to create a Signal Domain having a sequence which shows complementarity toward and is hybridizable to the Signal Template Domain of the Template Oligonucleotide.

The precise conditions of any given extension reaction depend on the particular DNA polymerase employed are known to one of skill in the art.

In a preferred embodiment, the exonuclease negative (exo⁻) Klenow fragment of *E. coli* DNA polymerase I (1 μl, 5 units) and α-$^{32}$P-dATP (6 μl, 10 μCi/μl, final concentration of 1 μM) are added to pre-annealed Substrate and Template Nucleic Acids in a total reaction volume of 10 μl (see Table 1 and Section 6.3 below). Preferably, highest available specific activity radio nucleotide is employed (currently 6000 Ci/mmol) to obtain the highest sensitivity probes.

TABLE 1

REACTION COMPONENTS

| Component | Concentration | Vol. | Final Concentration |
|---|---|---|---|
| Exo⁻ Klenow DNA Polymerase | 5 U/μl | 1 μl | 0.5 U/μl |
| α-$^{32}$P-dATP, 6000 Ci/mmol | 10 μCi/μl | 6 μl | 6 μCi/μl, 1 μM |
| Substrate Nucleic Acid | 0.5 mole | 1 μl | 50 nM |
| Template Nucleic Acid | 12.5 pmole | 1 μl | 1.25 μM |
| Reaction Buffer | 10× | 1 μl | 10 mM Tris pH 7.5 5 mM MgCl$_2$ 7.5 mM DTT |
| | | 10 μl Final Vol. | |

The present invention encompasses methods that may yield less than 90% labeling efficiency. When the labeling efficiency is less than 90%, the labeled nucleic acid is preferably isolated from the unlabeled nucleic acid. The difference between the sizes of the Substrate Nucleic Acid and the Probe allows the probe to be separated from the unlabeled Substrate Nucleic Acid by, for example, preparative polyacrylamide gel electrophoresis (PAGE). The Probe migrates at a slower rate on PAGE and can be identified by, for example, its radioactivity. The desired nucleic acid species are cut out of the gel and eluted by standard methods including, but not limited to, electro elution or crushing then soaking the gel slice in water or buffer.

In another embodiment, the Probe is a Complex that also includes the Template Nucleic Acid. The double stranded portion of the Complex will not interfere with the hybridization of the Target Binding Domain in subsequent assays. Optionally, after the Signal Domain is formed, the Probe is covalently cross-linked to the Template Nucleic Acid. Nucleic acid cross-linking agents suitable for the present invention include, but are not limited to, 4'-aminomethyltrioxsalen hydrochloride (Sigma-Aldrich, Milwaukee, Wis.), N-5-azido-2-nitrobenzoyloxysuccinimide, dimethyl adipimidate-2HCl, and dimethyl pimelimidate-2HCl (Pierce).

5.4 Polymerases for the Extension Reaction

In a preferred embodiment, the enzyme used to catalyze the primer extension labeling reaction (see FIG. 1B and FIG. 1C) is an exo⁻ Klenow fragment of *E. coli* DNA polymerase I. In alternative embodiments, other DNA polymerase enzymes can be used including viral (bacteriophage) DNA polymerases, thermophilic DNA polymerases (such as those used in PCR), and reverse transcriptase. These enzymes may be native, recombinant, or modified. Modifications of DNA polymerases contemplated by the methods of the present invention include but are not limited to modifications that remove activities activities other than polymerase activities, for example exonuclease activity. Suitable DNA polymerases for the primer extension reaction include but are not limited to *E. coli* DNA Polymerase I, T4 DNA polymerase, T7 DNA polymerase (native or modified), Taq DNA polymerase, or reverse transcriptase. One skilled in the art would be able to identify other polymerases suitable for the primer extension reaction of the present invention.

It is advantageous that the DNA polymerase used in the labeling reaction be a processive enzyme, as are those listed above. This ensures that the primer extension reaction is complete and that only the full-length extension product is formed.

5.5 Nucleotide Labels and Detection 5.5.1 Radioactivity

In certain embodiments, the labeled nucleotide incorporated into the Signal Domain is a radiolabeled nucleotide. In a preferred embodiment, the labeled nucleotide is α-$^{32}$P-dATP. However, any other labeling moiety that is adaptable to the present protocol can be used, as will be recognized by one of skill in the art. Commonly used radioactively labeled nucleotides for the practice in the invention include, but are not limited to, α-$^{32}$P-dNTP, α-$^{33}$P'-dNTP, and α-$^{35}$S-dNTP. As an alternative to radioactive labeling, non-radioactively labeled nucleotides can be used. For example, biotin-7-dATP functions interchangeably with α-$^{32}$P-dATP in the labeling reaction (see Section 7, below).

5.5.2 Fluorescence

In certain embodiments of the invention, the extension reaction incorporates a fluorescently labeled nucleotide into the Signal Domain. A fluorescently labeled nucleotide includes but is not limited to fluorescein-15-dATP, fluorescein-12-dUTP, tetramethylrhodamine-6-dUTP (Boehringer Mannheim), or Cy5-dCTP (Pharmacia). In a preferred embodiment, a the fluorescently labeled nucleotide is fluorescein-15-dATP.

5.5.3 Haptens and Enzymes

Nonisotopically labeled probes typically have a shelf life of over two years and much more DNA can be labeled in one reaction, providing a constant, quality controlled reagent for use in multiple experiments. Some examples of derivative dATP molecules that are not meant to be limiting to the scope of the present invention include, digoxigenin-16-dATP (Boehringer Mannheim), biotin-7-dATP (Sigma, St. Louis, Mo.), and biotin-21-dATP (Clontech).

One of the ways in which a nucleic acid or antibody can be detectably labeled is by linking the same to an enzyme and use in an enzyme immunoassay (EIA) (Voller, "The Enzyme Linked Immunosorbent Assay (ELISA)", 1978, Diagnostic Horizons 2:1–7, Microbiological Associates Quarterly Publication, Walkersville, Md.); Voller et al., 1978, J. Clin. Pathol. 31:507–520; Butler, 1981, Meth. Enzymol. 73:482–523; Maggio (ed.), 1980, Enzyme Immunoassay, CRC Press, Boca Raton, Fla.; Ishikawa et al., (eds.), 1981, Enzyme Immunoassay, Kgaku Shoin, Tokyo). The enzyme which is bound to the nucleic acid or antibody will react with an appropriate substrate, preferably a chromogenic substrate, in such a manner as to produce a chemical moiety which can be detected, for example, by spectrophotometric, fluorimetric or by visual means. Enzymes which can be used to detectably label the nucleic acid or antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

5.6 Kits

The present invention also provides a kit for the practice of the labeling methods of the invention. The kit comprises in one or more containers a Template Nucleic Acid (preferably universal labeling reagent) and one or more of the following: (i) 10× stock buffer (e.g. 100 mM Tris pH 7.5; 50 mM MgCl$_2$, 75 mM DTT) and a stop solution (10 mM EDTA)); (ii) RNA or DNA polymerase (most preferably the exo⁻ Klenow Fragment of E. coli DNA polymerase); (iii) a Template Hybridization Domain for ligating to a Target Binding Domain to generate a Substrate Nucleic Acid; (iv) a control Substrate Nucleic Acid and a control Target Nucleic Acid; and/or (v) a labeled nucleotide for use in the extension reaction and, optionally, if the label is a hapten, an antibody for detection, or if the label is an enzyme, colorimetric reagents for detection.

In a preferred embodiment, a kit of the invention comprises a reaction mixture comprising a Substrate Nucleic Acid and Template Nucleic Acid, and a DNA polymerase. Optionally, the kit further comprises a buffer, a stop buffer, a labeled nucleotide, a control substrate and control target nucleic acid, and/or reagents for the detection of a labeled nucleotide.

The following experimental examples are offered by way of illustration and not by way of limitation.

6. EXAMPLE 1

Efficiency of the Primer Extension Reaction with Substrate and Template Nucleic Acids

6.1 Materials and Reagents

The following reagents were used for polynucleotide (PNK) reactions: an oligonucleotide substrate; T4 PNK (NEW ENGLAND BIOLABS™); γ-$^{32}$P-ATP, 6000 Ci/mmol (Amersham); the buffer: 70 mM Tris pH 7.6, 10 mM MgCl$_2$, and 5 mM DTT; TE (10 mM Tris pH 8.0, 1 mM EDTA); and, distilled, deionized water.

The following reagents were used for primer extension reactions: a PAGE purified Substrate oligonucleotide with a 3' Binding Domain; PAGE purified Template Nucleic Acid; 10× stock buffer (100 mM Tris pH 7.5; 50 mM Mg Cl$_2$, 75 mM DTT); a stop solution (10 mM EDTA); 10 μM dATP (unlabeled); and exo⁻Klenow DNA polymerase (5 units/μl, NEW ENGLAND BIOLABS™).

Equipment and supplies included: 500 μl microfuge tubes; 1.5 ml screw cap microfuge tubes; SEPHADEX™ (G25 spin columns); a waterbath set to 94° C.; a waterbath set to 37° C.; a tabletop microcentrifuge; and a micropipette with aerosol barrier tips.

Nine distinct Template Nucleic Acids were employed that each contained a 6 (SEQ ID NO:8, 9, 10), 5 (SEQ ID NO: 11, 12, 13) or 4 (SEQ ID NO:14, 15, 16) base Substrate Hybridization Domain (FIG. 2A). These Template Nucleic Acids were modified such that the binding domain comprised dC (SEQ ID NO:8, 11, 14), 5-me-dC (SEQ ID NO:9, 12, 15), or C5-propynyl-dC (SEQ ID NO: 10, 13, 16). Each Template Nucleic Acid was blocked at the 3' end with an amino modifier-C$_7$ group (Glen Research).

The Substrate Nucleic Acid was a 36-mer comprised of a unique 30 nucleotide sequence at the 5'-end and a 6 base 3' Template Hybridization Domain (underlined): 5'-CT-TGATTAGGGTGATGGTTCACGTAGTGG<u>GGGCGGG</u>-3'. (SEQ ID NO: 17)

The purpose of this study was to define the efficiency of the primer extension reaction using the methods of the invention. It was therefore necessary to quantitatively compare unreacted substrate with reacted substrate. The protocol was modified so that radiolabel was incorporated at the 5'-end of the Substrate Nucleic Acid using T4 PNK and γ-$^{32}$P-ATP, and the subsequent primer extension reaction was conducted using unlabeled (cold) dATP, thereby allowing both reacted and unreacted Substrate nucleic acid to be detected.

6.2 Labeling Nucleic Acids Using T4 Kinase

The Substrate Nucleic Acid was resuspended in TE at a final concentration of 0.5 μM (0.5 picomoles/μl. From this stock, 2 picomoles (4 μl) was 5' end labeled using T4 PNK. The Substrate Nucleic Acid was incubated with 100 μCi γ-$^{32}$P-ATP and 5 units of T4 PNK in a final reaction volume of 50 μl with kinase buffer of composition as described above for 1 hour at 37° C. Unincorporated γ-$^{32}$P-ATP was removed by passage through a SEPHADEX™ G-25 spin column. Radiolabel incorporation was measured using scintigraphy.

5'-$^{32}$P-end-labeled Substrate Nucleic Acid (prepared as described above) was "spiked" into an aliquot of cold Substrate at 10,000 CPM/μl (approximately 1 femtomole of radiolabeled compound per 0.5 picomole cold oligonucleotide). All reagents were stored at −20° C. and kept in an ice bucket at 0° C. until thawed for use.

6.3 Primer Extension Reaction

The primer extension protocol involved two steps: annealing the Substrate and Template Nucleic Acids, and a primer extension reaction. Following the extension reaction, the reaction products were separated using analytical PAGE. The Probe was Visualized using phosphorimaging.

1 μl of Substrate Nucleic Acid, 1 μl of 10× stock reaction buffer, and 1 μl of Template Nucleic Acid (resuspended at 12.5 μM concentration in TE (12.5 picomoles per μl)) were added together in a 500 μl microcentrifuge tube in the molar concentrations shown in Table 2 (see FIG. 1B). The reaction was mixed without vortexing by pipetting up and down. The tube was then placed in a hot water bath at 94° C. for 1 minute. The tube was removed from heat and the annealing reaction proceeded in the same tube for 5 minutes, slowly cooling to room temperature. The tube was then centrifuged briefly to return the contents to the bottom of the tube, which ensured that all nucleic acid and buffer was available for the primer extension reaction.

TABLE 2

| ANNEALING | | |
| --- | --- | --- |
| Reagent | Amount | Volume |
| Substrate Nucleic Acid | 0.5 pmole (10,000 CPM) | 1 μl |
| Template Nucleic Acid | 12.5 pmole | 1 μl |
| Reaction Buffer | 10 × Stock | 1 μl |
| Final Volume | | 3 μl |

1 μl of 10 μM cold dATP, 5 μl of water, and 1 μl of exo Klenow fragment of E. coli DNA polymerase I were added directly into the previously prepared annealing tube and mixed, as in Table 3, using an up and down pipetting action with an aerosol barrier pipette tip. The reaction was allowed to proceed at room temperature for one hour (FIG. C). The reaction was stopped with the addition of an equal volume (10 μl) of gel loading buffer (7M urea. 100 mM EDTA), heated at 94° C. for 5 minutes, and separated on a 12% polyacrylamide, 7M urea, 0.5×TBE (45 mM Tris borate, 1 mM EDTA) gel. The gel was exposed to a Packard MP Phosphor Screen for 2 hours and visualized using a Packard Cyclone™ Storage Phosphor System.

TABLE 3

LABELING REACTION

| Reagent | Volume | Final Concentration |
| --- | --- | --- |
| Substrate Nucleic Acids, Template Nucleic Acid Buffer | 3 µl | 50 nM Substrate 1.25 µM Template 1× Buffer |
| Exo⁻ Klenow DNA | 1 µl | 0.5 U/µl |
| 10 µM dATP | 1 µl | 1 µM |
| H$_2$O | 5 µl | |
| | 10 µl final vol. | |

The Substrate Nucleic Acid, the Template and final reaction products are as follows ("A":=dA residues added by primer extension; "C"=dC, 5-me-dC, or C5-propynyl-dC; "#"=3'-amino-modifier-C$_7$):

```
Substrate Nucleic Acid (SEQ ID NO.18):
5'-³²P-CTTGATTAGGGTGATGGTTCACGTAGTGGGGGCGGG-3'

Template Nucleic Acid (SEQ ID NOS:8-16):
3'-#-CCGCCCTTTTTTTTTT-5'

Probe (SEQ ID NO:19):
5'-³²P-CTTGATTAGGGTGATGGTTCACGTAGTGGGGGCGGGAAAAAAAAAA-3'
                                         ::::::::::::::::
                                      3'-#-CCGCCCTTTTTTTTTT-5'
```

In this example, the original 36-mer Substrate Nucleic Acid was increased in length to 46 bases by the printer extension reaction. The extension efficiency was determined by comparing the amount of nucleic acid signal remaining as a 36-mer (FIG. 2B) to the amount of nucleic acid increased in length to the 46-mer. These values were quantitatively determined by integrating pixel density (ImageQuant™ Software, Packard Instrument Company) from images obtained using a Packard Cyclone™ Storage Phosphor System and are summarized graphically in FIG. 3. Without heterocyclic base modification introduced in the binding domain of the Template Nucleic Acid, a binding domain of 6 bases is necessary to obtain more than 80% extension of the Substrate. The extension efficiency drops significantly when the binding domain is decreased to 5 nucleic acids and even more so at a length of 4 nucleic acid residues. If 5-me-dC or, even better, C5-propynl-dC are substituted for deoxycytidine (dC) in the binding domain of the Template Nucleic Acid, the extension efficiency increases. This effect is most evident with a binding domain 5 residues long.

7. EXAMPLE 2

Comparison of Sensitivity of Probes Labeled Using T4 and Primer Extension

7.1 Materials and Reagents

Reagents and materials used to label the Substrate Nucleic Acid at the 5' end using T4 PNK and at the 3' end by primer extension were identical to those previously described in Example 1 (Section 6, supra). with the exception that α-$^{32}$P-dATP (6000 Ci/mmol, Amersham) was substituted for unlabeled dATP in the primer extension reaction.

In this example, based on kit format, both the Substrate Nucleic Acid, a 36-mer, and Template Nucleic Acid a 16-mer, are provided lyophilized. The Substrate Nucleic Acid is the same as used in Example 1 and contains a 30 base specific sequence at the 5' end complementary to the target plasmid pGreenLantern™-1 and a 6 base 3' end Template Hybridization Domain, GGCGGG (SEQ ID NO:1). The Template Nucleic Acid consists of a 10 base oligo-dT sequence Signal Template Domain at the 5'-end, a 6 base 3' Substrate Hybridization Domain complementary to the Template Hybridization Domain of the Substrate Nucleic Acid, and is 3'-end blocked with an amino-modifier-C$_7$ group.

The Substrate Nucleic Acid is: 5'-CTTGATTAGGGT-GATGGTTCACGTAGTGGG<u>GGCGGG</u> 3' (SEQ ID NO:17). The underlined portion is the Template Hybridization Domain. The Template Nucleic Acid is: 5'-TTTTTTTTTT<u>CCCGCC</u>-C$_7$-amino-modifier-3' (SEQ ID NO:10), where <u>C</u> represents C5-propynyl-dC.

The Template Nucleic Acid was resuspended in TE at a concentration of 12.5 µM (12.5 picomoles per µl). A stock solution of the Substrate Nucleic Acid was made in TE at a concentration of 10 µM (10 picomoles per µl). A working solution of the Substrate was made by 1:20 dilution in distilled water with a final concentration of 0.5 µM (0.5 picomoles per µl). All reagents were stored at −20° C. and kept in an ice bucket at 0° C. until thawed for use. It is preferable to make a series of aliquots of these reagents upon receipt of the kit in single use tubes for both contamination control and ease of use.

7.2 Labeling with T4 Polynucleotide Kinase

From the 10 µM stock of Substrate Nucleic Acid, 2 picomoles (2 µl) was 5'-end labeled using T4 PNK, as described in Example 1 (Section 6.2, supra). Briefly, Substrate Nucleic Acid was incubated with 100 µCi γ-$^{32}$P-ATP and 5 units of T4 PNK in a final reaction volume of 50 µl with kinase buffer of composition as described for 1 hour at 37° C. Unincorporated γ-$^{32}$P-ATP was removed by passage through a SEPHADEX™ G-spin column. Radiolabel incorporation was measured using scintigraphy and, assuming no loss of labeled nucleic acid or contamination with unincorporated label, resulted in a specific activity of 1×10$^7$ CPM per picomole probe. Structure of this labeled probe is shown in FIG. 4A.

7.3 Nucleic Acid Labeling by Primer Extension

The labeling protocol involved two steps: annealing the Substrate and Template Nucleic Acid (~10 minutes), and a primer extension reaction (1 hour) and was followed by removal of unincorporated label (~10 minutes).

The annealing step of the primer extension reaction was carried out as described in Example 1 (Section 6.3, supra). Briefly, 1 µl (0.5 picomoles) of Substrate Nucleic Acid (from the dilute "working solution"), 1 µl of 10× reaction buffer, and 1 μl (12.5 picomoles) of Template Nucleic Acid were added together in a 500 μl microcentrifuge tube in the same molar concentrations as shown in Table 2. After heating the sample to 94° C. (1 minute) and cooling to room temperature (5 minutes), 6 μl of α-$^{32}$PdATP and 1 μl (5 units) of the exo Klenow fragment of E. coli DNA polymerase were added. The reaction was allowed to proceed at room temperature for one hour. 40 μl of stop solution (10 mM EDTA) was added and the reaction was passed through a SEPHADEX™ G25 spin column to remove unincorporated α$^{32}$pdATP. An aliquot was removed and evaluated for radiolabel incorporation by liquid scintillation counting. Assuming no loss of labeled nucleic acid or contamination with unincorporated label, the probe had a specific activity of 9×10$^7$ CPM per picomole, nearly 10× that of the probe labeled with PNK. The structure of the labeled probe produced is shown in FIG. 4A.

7.4 Comparison of Probe Sensitivities in a Dot Blot Assay

To directly compare the functional sensitivity of a 5' end-labeled probe and a 3' primer-extension labeled probe using the method of the invention, two identical dot blots were prepared using a commercially available plasmid as target, pGreen Lantern™-1. Decreasing mass amounts of plasmid, including 100 attomoles, 10 attomoles, and 1 attomole, were spotted onto MSI nylon transfer membranes (Micron Separations, Inc.), denatured in 0.5 M NaOH, 1.5 M NaCl for 30 minutes, renatured in 1.0 M Tris pH 7.5, 1.5 M NaCl for 30 minutes, and baked at 80° C. for 1 hour. The membranes were prehybridized in 0.9 M NaCl, 0.18 M Tris pH 7.5, 0.012 M EDTA, 5× Denhardt's solution, and 100 μg/ml sheared denatured salmon sperm DNA at 60° C. for 2 hours, Hybridization was carried out overnight in 15 volume of the prehybridization solution with 10$^7$ CPM of probe added (final 7×10$^5$ CPM/ml). Probes were hybridized to separate blots in parallel. Blots were washed in 5×SSC (0.75 M NaCl, 0.075 M NaCitrate) at 50° C. for 30 minutes. Blots were exposed to a Packard MP Phosphor Screen for two hours and visualized using a Packard Cyclone™ Storage Phosphor System.

The results, shown in FIG. 4B, demonstrate that the probe labeled using the method of the present invention has a sensitivity in a dot blot hybridization assay about 10-fold greater than that of a 5'end-labeled probe. Thus functional activity in a practical application directly parallels the predicted results based upon the measured specific activity of each probe and directly demonstrates the utility of the invention.

7.5 Non-Isotopic Labeling

Substrate Nucleic Acid (SEQ ID NO:17) and Template Nucleic Acid were labeled using the primer extension method of the invention as outlined above in Section 7.3. α-$^{32}$P-dATP was replaced with biotin-7-dATP label at a final concentration of 10 μM. The reaction proceeded normally and resulted in a highly modified biotin labeled probe. The biotin labeled probe was hybridized in a dot blot assay as described in Section 7.4 above, in which it successfully detected its target.

8. EXAMPLE 3

Comparison of Sensitivity of Probes Labeled by Primer Extension and by T4 Polynucleotide Kinase in a Northern Blot Assay 8.1 Materials and Reagents Reagents and materials used to label the Substrate Nucleic Acid at the 5' end using T4 PNK and at the 3' end by primer extension were identical to the methods previously described in Example 2 (Section 7, supra). In this example the Substrate Nucleic Acid, a 36-mer, and Template Nucleic Acid, a 16-mer, are again provided lyophilized. The Substrate Nucleic Acid contains a 30 base specific sequence at the 5' end complementary to the human β-actin mRNA and the standard 6-base 3' end Template Hybridization Domain. The Template Nucleic Acid is comprised of a 10-base oligo-dT Signal Template Domain sequence at the 5'-end, a 6-base 3' Substrate Hybridization Domain complementary to the Template Hybridization Nucleic Acid Domain of the Substrate, and is blocked with a 3'-amino-modifier-C7 group.

The Substrate Nucleic Acid is: 5, -GCCCAGGAAG-GAAGGCTGGAAGAGTGCCTC<u>GGCGGG</u>-3' (SEQ ID NO:20), where the underlined portion is the Template Binding Domain. The Template Nucleic Acid is: 5'-TTTTTTTTTT<u>CCCGCC</u>-C7-amino-modifier-3' (SEQ ID NO:10), where <u>C</u> represents C5-propynyl-dC.

The Template Nucleic Acid was resuspended in TE at a concentration of 12.5 μM (12.5 picomoles per μl). A stock solution of the Substrate Nucleic Acid was made in TE at a concentration of 10 μM (10 picomoles per μl). A working solution of the Substrate was made by 1:20 dilution in distilled water with a final concentration of 0.5 μM (0.5 picomoles per μl). All reagents were stored at −20° C. and kept in an ice bucket at 0° C. until thawed for use. It is preferable to make a series of aliquots of these reagents upon receipt of the kit in single use tubes for both contamination control and ease of use.

8.2 Labeling with T4 Polynucleotide Kinase

From the 10 μM stock of Substrate Nucleic Acid, 2 picomoles (2 μl) was 5'-end labeled using T4 polynucleotide kinase, as described in Example 2 (Section 7.2, supra). Substrate Nucleic Acid was incubated with 100 μCi γ-$^{32}$P-ATP and 5 units of T4 PNK in a final reaction volume of 50 μl with kinase buffer for 1 hour at 37° C. Unincorporated γ-$^{32}$P-ATP was removed by passage through a SEPHADEX™ G-25 spin column. Radiolabel incorporation was measured using scintigraphy and, assuming no loss of labeled nucleic acid or contamination with unincorporated label, resulted in a specific activity of 8×106 CPM per picomole probe. Structure of this labeled probe is shown in FIG. 5A.

8.3 Nucleic Acid Labeling by Primer Extension

The annealing step of the primer extension reaction was carried out as described previously. Briefly, 1 μl (0.5 picomoles) of Substrate Nucleic Acid (0.5 μM stock), 1 μl of 10× reaction buffer, and 1 μl (12.5 picomoles) of Template Nucleic Acid were added together in a 500 μl microcentrifuge tube. After heating the sample to 94° C. (1 minute) and cooling to room temperature (5 minutes), 6 μl of α-$^{32}$P dATP and 1 μl (5 units) of the exo Klenow fragment of E. coli DNA polymerase were added. The reaction was allowed to proceed at room temperature for one hour. 40 μl of stop solution (10 mM EDTA) was added and the reaction was passed through a SEPHADEX™ G25 spin column to remove unincorporated α-$^{32}$P-dATP. An aliquot was removed and evaluated for activity by liquid 30 scintillation counting. Assuming no loss of labeled nucleic acid or contamination with unincorporated label, the probe had a specific activity of 7×10$^7$ CPM per picomole, about 10 times that of the probe labeled with PNK. The structure of the labeled probe produced is shown in FIG. 5A.

8.4 Comparison of Probe Sensitivities in a Northern Blot Assay

To directly compare the functional sensitivity of a PNK 5' end-labeled probe and a 3' primer-extension labeled probe using the method of the invention, two identical Northern blots were prepared using human placental RNA. Ten micrograms of total RNA (AMBION™) was separated on a formaldehyde-agarose gel (Current Protocols in Molecular Biology, John Wiley & Sons, Inc.). After electrophoresis, RNA was transferred to MSI nylon membranes (Micron Separations, Inc.) by capillary action in 20× SSC and baked at 80° C. for 1 hour. The membranes were prehybridized in PerfectHyb™ (Sigma) at 60° C. for one hour. Hybridization was carried out for 4 hours at 60° C. in 10 mls total volume of PerfectHyb™ with 107 CPM of probe added (final 106 CPM/ml). Probes were hybridized to separate blots in parallel. Blots were washed twice in 5×SSC (0.75 M NaCl, 0.075 M NaCitrate) at 55° C. for 30 minutes. Blots were exposed to a Packard MP Phosphor Screen for one hour and visualized using a Packard Cyclone™ Storage Phosphor System.

The results, shown in FIG. 5B, demonstrate that the probe labeled using the method of the present invention has greater sensitivity in a Northern blot hybridization assay than a 5'end-labeled probe. Thus functional activity in a second application shows improved sensitivity using a high specific activity probe and directly demonstrates the utility of the invention.

9. EXAMPLE 4:

Use of the Primer Extension Labeling Method with an RNA Substrate Nucleic Acid

9.1 Materials and Reagents

Reagents and methods used to label an oligoribonucleotide at the 5'-end with PNK were identical to those used to label oligodeoxyribonucleotides in Example 1 (Section 6, Supra).

In this example, two Substrate Nucleic Acids, one DNA and one RNA, were labeled by the method of the invention. The oligodeoxyribonucleotide employed was 5'-GCCCAG-GAAGGAAGGCTGGAAGAGTGCCTC GGCGGG-3'(SEQ ID NO:20), a 36-mer comprised of a unique 30 nucleotide sequence at the 5'-end and a 6-base 3' Template Hybridization Domain (underlined). The oligoribonucleotide employed was 5'-cugggcauggaguccugug-gcauccacgaaacuaccggcggg-3' (SEQ ID NO:23), a 46-mer comprised of a unique 40 nucleotide sequence at the 5'-end and a 6-base 3' Template Hybridization Domain (underlined). One oligodeoxyribonucleotide Template Nucleic Acid was employed fore both reactions, 5'-TTTTTTTTTTpCpCpCGpCpC-C$_7$-amino-modifier-3' (SEQ ID NO:10).

To obtain a quantitative visualization of Substrate utilization, radiolabel was incorporated at the 5'-end of the Substrate Nucleic Acids using T4 PNK and γ-$^{32}$P-ATP. The subsequent primer extension reaction was conducted using unlabeled (cold) dATP, as described in Example 1 (Section 6 above).

9.2 Labeling Nucleic Acids Using T4 Kinase

The Substrate Nucleic Acids were resuspended in TE at a final concentration of 0.5 μM (0.5 picomoles/μl). From this stock, 2 picomoles (4 μl) was 5' end labeled using T4 PNK. Substrate Nucleic Acids were each incubated with 100 μCi γ-$^{32}$P-ATP and 5 units of T4 PNK in a final reaction volume of 50 μl with kinase buffer for 1 hour at 37° C. Unincorporated γ-$^{32}$P-ATP was removed by passage through a SEPHADEX™ G-spin column. Radiolabel incorporation was measured using scintigraphy.

The Template Nucleic Acid was resuspended at 12.5 μM concentration in TE (12.5 picomoles per μl). 5'-$^{32}$P-end-labeled Substrate Nucleic Acids (prepared as described above) were "spiked" into aliquots of cold Substrate at 10,000 CPM/μl (approximately 1 femtomole of radiolabeled compound per 0.5 picomole cold oligonucleotide). All reagents were stored at –20° C. and kept in an ice bucket at 0° C. until thawed for use.

9.3 Primer Extension Reaction

The primer extension protocol involved two steps, annealing the Substrate and Template Nucleic Acids and extending the Substrate Nucleic Acid in a primer extension reaction. Following the extension reaction, the reaction products were separated using analytical PAGE followed by visualization using phosphorimaging.

1 μl of Substrate Nucleic Acid, 1 μl of 10× stock reaction buffer, and 1 μl of Template Nucleic Acid were added together in a 500 μl microcentrifuge tube in the molar concentrations shown in Table 2 (see FIG. 1B). The reaction was mixed without vortexing by pipetting up and down. The tube was then placed in a hot water bath at 94° C. for 1 minute. The tube was removed from heat and the annealing reaction proceeded in the same tube for 5 minutes, slowly cooling to room temperature. The tube was then centrifuged briefly to return the contents to the bottom of the tube, which ensured that all nucleic acid and buffer was available for the primer extension reaction.

1 μl of 101M unlabeled dATP, 5 μl of water, and 1 μl of exo-Klenow fragment of E. coli DNA polymerase I were added directly into the previously prepared annealing tube and mixed using an up and down pipetting action with an aerosol barrier pipette tip. The reaction was allowed to proceed at room temperature for one hour (FIG. 1C). The reaction was stopped with the addition of an equal volume (10 μl) of gel loading buffer (7M urea, 100 mM EDTA), heated at 94° C. for 5 minutes, and separated on a 12% polyacrylamide, 7M urea, 0.5×TBE (45 mM Tris borate, 1 mM EDTA) gel. The gel was exposed to a Packard MP Phosphor Screen for 2 hours and visualized using a Packard Cyclone™ Storage Phosphor System. In this example, the 5'-end labeled 36-mer DNA Substrate Nucleic Acid 5'-$^{32}$P-GCCCAGGAAGGAAGGCTGGAAGAGTGC-CTCGGCGGG-3' (SEQ ID NO:21) is increased in length to 46 bases, 5'-$^{32}$P-GCCCAGGAAGGAAGGCTGGAA-GAGTGCCTCGGCGGGAAAAAAAAAA-3' (SEQ ID NO:22). The 5'-end labeled 46-mer RNA Substrate Nucleic Acid, 5'-$^{32}$P-cugggcauggaguccuguggcauccac-gaaacuaccuucaggcggg-3' (SEQ ID NO:24), is increased in length to 56 bases by the primer extension reaction to 5'-$^{32}$P-cugggcauggaguccuguggcauccac-gaaacuaccuucaggcgggAAAAAAAAAA-3' (SEQ ID NO:25), as shown in FIG. 6A. The extension efficiency was determined by comparing the amount of signal visualized in each product by phosphorimaging, as shown in FIG. 6B. These values were quantitatively determined by integrating pixel density (ImageQuant™ Software, Packard Instrument Company) from images obtained using a Packard Cyclone™ Storage Phosphor System. Approximately 90% of the DNA substrate was extended in the primer extension reaction while just over 70% of the RNA substrate was extended in the primer extension reaction. The methods described herein, therefore, can be used to label RNA Substrate Nucleic Acids.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method of labeling an oligonucleotide, comprising the steps of:
   (a) hybridizing a first oligonucleotide to a second oligonucleotide, wherein the first oligonucleotide consists of, from 3' to 5': a Substrate Hybridization Domain adjoining a Signal Template Domain, wherein:
      the Substrate Hybridization Domain consists of a sequence of about 5 to about 20 nucleotides and cannot be extended by a 5'→3' DNA polymerase; and
      the Signal Template Domain consists of a sequence of about 5 to about 100 nucleotides;
   and the second oligonucleotide comprises; from 3' to 5': a Template Hybridization Domain adjoining a Target Binding Domain, wherein:
      the Template Hybridization Domain consists of a sequence of about 5 to about 20 nucleotides which is not detectably labeled, has 5 or more bases complementary to the Substrate Hybridization Domain of the first oligonucleotide, and is hybridizable to the Substrate Hybridization Domain of the first oligonucleotide; and
      the Target Binding Domain is not detectably labeled and comprises a nucleotide sequence heterologous to that of the Template Hybridization Domain and to that of the first oligonucleotide; and
   (b) extending the second oligonucleotide with a DNA polymerase in the presence of labeled nucleotides to create an oligonucleotide Probe having from 5' to 3' an unlabeled Target Binding Domain adjoining a Template Hybridization Domain adjoining a labeled Signal Domain.

2. The method of claim 1, wherein the first or second oligonucleotide consists of deoxyribonucleotides.

3. The method of claim 1, wherein the first or second oligonucleotide consists of ribonucleotides.

4. The method of claim 1, wherein the second oligonucleotide consists of about 15 to about 150 nucleotides.

5. The method of claim 1, wherein the 3' nucleotide of the Substrate Hybridization Domain is a 3'-terminal modified nucleotide.

6. The method of claim 5, wherein the modification is selected from the group consisting of: a 3'-amino-modifier, a 2',3'-dideoxynucleotide, a 3'-phosphate, and a modified 3'-phosphate group.

7. The method of claim 1, wherein the 3' nucleotide of the Substrate Hybridization Domain is a modified cytidine selected from the group consisting of: C5 methyl-dC and C5-propynyl-dC.

8. The method of claim 1, wherein the Signal Template Domain consists of about 10 to about 50 nucleotides.

9. The method of claim 1, wherein the Signal Domain is at least 50% homopolymeric.

10. The method of claim 9, wherein at least 60% of the nucleotides of the Template Hybridization Domain comprise guanosine or cytidine or a combination thereof, and the Signal Domain is at least 50% homopolymeric.

11. The method of claim 1, wherein the extending step is carried out by a DNA polymerase selected from the group consisting of: E. coli DNA polymerase I holoenzyme, Klenow fragment of E. coli DNA polymerase I, T4 DNA polymerase, T7 DNA polymerase, and a DNA polymerase encoded by a thermophilic bacterium.

12. The method of claim 1, wherein one or more of the nucleotides of the Template Hybridization Domain or the Substrate Hybridization Domain is a modified nucleotide, which modified nucleotide increases the hybridization affinity of said Template Hybridization Domain to said Substrate Hybridization Domain.

13. The method of claim 12, wherein at least one modified nucleotide is found in the Template Hybridization Domain.

14. The method of claim 13, wherein at least one modified nucleotide is selected from the group consisting of: C5-methyl-dC, C5-propynyl-dC, C5-propynyl-dU, and 2.6 diaminopurine.

15. The method of claim 1, wherein at least one nucleotide is labeled with a label selected from the group consisting of: $^{32}P$, $^{33}P$, $^{35}S$, fluorescein, digoxigenin, biotin, Cy5, Cy3, and rhodamine.

16. The method of claim 1, wherein the oligonucleotide Probe has a specific activity of $7 \times 10^7$ CPM per picomole.

17. The method of claim 1, wherein the oligonucleotide Probe has a specific activity of $9 \times 10^7$ CPM per picomole.

18. The method of claim 1, wherein the Signal Domain Is at least 70% homopolymeric.

19. The method of claim 1, wherein the Signal Domain is at least 90% homopolymeric.

20. The method of claim 1, wherein the Signal Domain is 100% homopolymeric.

21. The method of claim 1, wherein the Substrate Hybridization Domain consists of a sequence of from about 5 to about 10 nucleotides and wherein the Template Hybridization Domain consists of a sequence of from about 5 to about 10 nucleotides.

22. The method of claim 1, wherein the second oligonucleotide consists essentially of a sequence of about 15 to about 150 nucleotides.

23. A method of labeling an oligonucleotide, comprising the steps of:
   (a) hybridizing a first oligonucleotide to a second oligonucleotide, wherein the first oligonucleotide consists of, from 3' to 5', a 3' nucleotide overhang adjoining a Substrate Hybridization Domain adjoining a Signal Template Domain, wherein:
      the Substrate Hybridization Domain consists of a sequence of about 5 to about 10 nucleotides and cannot be extended by a 5'→3' DNA polymerase; and
      the Signal Template Domain consists of a sequence of about 5 to about 100 nucleotides;
      and the second oligonucleotide comprises, from 3' to 5':
      a Template Hybridization Domain adjoining a Target Binding Domain, wherein:
      the Template Hybridization Domain consists of a sequence of about 5 to about 10 nucleotides, is not detectably labeled, and has at least 5 bases complementary to the Substrate Hybridization Domain of the first oligonucleotide;
      the Target Binding Domain is not detectably labeled and comprises a nucleotide sequence heterologous to that of the Template Hybridization Domain; and
   (b) extending the second oligonucleotide with a DNA polymerase in the presence of labeled nucleotides to form an oligonucleotide probe having from 5' to 3' an unlabeled Target Binding Domain adjoining a Template Hybridization Domain adjoining a labeled Signal Domain,
   wherein the overhang on the first oligonucleotide blocks extension of the first oligonucleotide by the DNA polymerase.

* * * * *

UNITED STATES PATENT AND TRADEMARK OFFICE
CERTIFICATE OF CORRECTION

PATENT NO.         : 7,135,284 B1
APPLICATION NO.  : 09/497943
DATED                  : November 14, 2006
INVENTOR(S)         : Mark Aaron Behlke et al.

It is certified that error appears in the above-identified patent and that said Letters Patent is hereby corrected as shown below:

Title Page column 1, inventor "Shale Anthony James" should read --Shale Anthony Dames--.

Signed and Sealed this

Eleventh Day of March, 2008

JON W. DUDAS
*Director of the United States Patent and Trademark Office*

SEQUENCE LISTING

<160> NUMBER OF SEQ ID NOS: 25

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1 ggcggg                                                                    6

<210> SEQ ID NO 2
<211> LENGTH: 6
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2 gggggg                                                                    6

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3 cccccc                                                                    6

<210> SEQ ID NO 4
<211> LENGTH: 20
<212> TYPE: DNA
<213> ORGANISM: Artificial Sequence
<220> FEATURE:
<221> NAME/KEY: modified_base
<222> LOCATION: (1)..(20)
<223> OTHER INFORMATION: N = A, C, G, or T
<223> OTHER INFORMATION: Description of Artificial Sequence:
      Oligonucleotide

<400> SEQUENCE: 4
nnnnnnnnnn nnnnnnnnnn                                                    20

<210> SEQ ID NO 5
<211> LENGTH: 26
<212> TYPE: DNA
<213> ORGANISM: Artificial Sequence
<220> FEATURE:
<221> NAME/KEY: modified_base
<222> LOCATION: (1)..(20)
<223> OTHER INFORMATION: N = A, C, G, or T
<223> OTHER INFORMATION: Description of Artificial Sequence:
      Oligonucleotide

<400> SEQUENCE: 5
nnnnnnnnnn nnnnnnnnnn ggcggg                                             26

<210> SEQ ID NO 6
<211> LENGTH: 10
<212> TYPE: DNA

```
<213> ORGANISM: Artificial Sequence
<220> FEATURE:
<223> OTHER INFORMATION: Description of Artificial Sequence:
      Oligonucleotide

<400> SEQUENCE: 6
tttttttttt                                                           10

<210> SEQ ID NO 7
<211> LENGTH: 7
<212> TYPE: DNA
<213> ORGANISM: Artificial Sequence
<220> FEATURE:
<221> NAME/KEY: modified_base
<222> LOCATION: (7)
<223> OTHER INFORMATION: N = C7-AMINO-MODIFIER, 3'
<223> OTHER INFORMATION: Description of Artificial Sequence:
      Oligonucleotide

<400> SEQUENCE: 7 cccgccn                                                               7

<210> SEQ ID NO 8
<211> LENGTH: 17
<212> TYPE: DNA
<213> ORGANISM: Artificial Sequence
<220> FEATURE:
<221> NAME/KEY: modified_base
<222> LOCATION: (17)
<223> OTHER INFORMATION: N = C7-AMINO-MODIFIER, 3'
<223> OTHER INFORMATION: Description of Artificial Sequence:
      Oligonucleotide

<400> SEQUENCE: 8
tttttttttt cccgccn                                                   17

<210> SEQ ID NO 9
<211> LENGTH: 17
<212> TYPE: DNA
<213> ORGANISM: Artificial Sequence
<220> FEATURE:
<221> NAME/KEY: modified_base
<222> LOCATION: (11)..(13)
<223> OTHER INFORMATION: N = 5-METHYL-2'-DEOXYCYTOSINE
<221> NAME/KEY: modified_base
<222> LOCATION: (15)..(16)
<223> OTHER INFORMATION: N = 5-METHYL-2'-DEOXYCYTOSINE
<221> NAME/KEY: modified_base
<222> LOCATION: (17)
<223> OTHER INFORMATION: N = C7-AMINO-MODIFIER, 3'
<223> OTHER INFORMATION: Description of Artificial Sequence:
      Oligonucleotide

<400> SEQUENCE: 9
tttttttttt nnngnnn                                                   17

<210> SEQ ID NO 10
<211> LENGTH: 17
<212> TYPE: DNA
<213> ORGANISM: Artificial Sequence
<220> FEATURE:
<221> NAME/KEY: modified_base
<222> LOCATION: (11)..(13)
<223> OTHER INFORMATION: N= 5-PROPYNYL-2'-DEOXYCYTOSINE
<221> NAME/KEY: modified_base
<222> LOCATION: (15)..(16)
<223> OTHER INFORMATION: N = 5-PROPYNYL-2'-DEOXYCYTOSINE
<221> NAME/KEY: modified_base
<222> LOCATION: (17)
<223> OTHER INFORMATION: N = C7-AMINO-MODIFIER
<223> OTHER INFORMATION: Description of Artificial Sequence:
```

Oligonucleotide

<400> SEQUENCE: 10
tttttttttt nnngnnn                   17

<210> SEQ ID NO 11
<211> LENGTH: 16
<212> TYPE: DNA
<213> ORGANISM: Artificial Sequence
<220> FEATURE:
<221> NAME/KEY: modified_base
<222> LOCATION: (16)
<223> OTHER INFORMATION: N = C7-AMINO-MODIFIER, 3'
<223> OTHER INFORMATION: Description of Artificial Sequence:
      Oligonucleotide

<400> SEQUENCE: 11
tttttttttt cccgcn                    16

<210> SEQ ID NO 12
<211> LENGTH: 16
<212> TYPE: DNA
<213> ORGANISM: Artificial Sequence
<220> FEATURE:
<221> NAME/KEY: modified_base
<222> LOCATION: (11)..(13)
<223> OTHER INFORMATION: N = 5-METHYL-2'-DEOXYCYTOSINE
<221> NAME/KEY: modified_base
<222> LOCATION: (15)
<223> OTHER INFORMATION: N = 5-METHYL-2'-DEOXYCYTOSINE
<221> NAME/KEY: modified_base
<222> LOCATION: (16)
<223> OTHER INFORMATION: N = C7-AMINO-MODIFIER, 3'
<223> OTHER INFORMATION: Description of Artificial Sequence:
      Oligonucleotide

<400> SEQUENCE: 12
tttttttttt nnngnn                    16

<210> SEQ ID NO 13
<211> LENGTH: 16
<212> TYPE: DNA
<213> ORGANISM: Artificial Sequence
<220> FEATURE:
<221> NAME/KEY: modified_base
<222> LOCATION: (11)..(13)
<223> OTHER INFORMATION: N = 5-PROPYNYL-2'-DEOXYCYTOSINE
<221> NAME/KEY: modified_base
<222> LOCATION: (15)
<223> OTHER INFORMATION: N = 5-METHYL-2'-DEOXYCYTOSINE
<221> NAME/KEY: modified_base
<222> LOCATION: (16)
<223> OTHER INFORMATION: N = C7-AMINO-MODIFIER
<223> OTHER INFORMATION: Description of Artificial Sequence:
      Oligonucleotide

<400> SEQUENCE: 13
tttttttttt nnngnn                    16

<210> SEQ ID NO 14
<211> LENGTH: 15
<212> TYPE: DNA
<213> ORGANISM: Artificial Sequence
<220> FEATURE:
<221> NAME/KEY: modified_base
<222> LOCATION: (15)
<223> OTHER INFORMATION: N = C7 AMINO-MODIFIER, 3'
<223> OTHER INFORMATION: Description of Artificial Sequence:
      Oligonucleotide

<400> SEQUENCE: 14

```
tttttttttt cccgn                                                     15
```

```
<210> SEQ ID NO 15
<211> LENGTH: 15
<212> TYPE: DNA
<213> ORGANISM: Artificial Sequence
<220> FEATURE:
<221> NAME/KEY: modified_base
<222> LOCATION: (15)
<223> OTHER INFORMATION: N = C7-AMINO-MODIFIER, 3'
<221> NAME/KEY: modified_base
<222> LOCATION: (11)..(13)
<223> OTHER INFORMATION: N = 5-METHYL-2'-DEOXYCYTOSINE
<223> OTHER INFORMATION: Description of Artificial Sequence:
      Oligonucleotide

<400> SEQUENCE: 15
tttttttttt nnngn                                                     15
```

```
<210> SEQ ID NO 16
<211> LENGTH: 15
<212> TYPE: DNA
<213> ORGANISM: Artificial Sequence
<220> FEATURE:
<221> NAME/KEY: modified_base
<222> LOCATION: (11)..(13)
<223> OTHER INFORMATION: N = 5-PROPYNYL-2'-DEOXYCYTOSINE
<221> NAME/KEY: modified_base
<222> LOCATION: (15)
<223> OTHER INFORMATION: N = C7-AMINO-MODIFIER, 3'
<223> OTHER INFORMATION: Description of Artificial Sequence:
      Oligonucleotide

<400> SEQUENCE: 16
tttttttttt nnngn                                                     15
```

```
<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
cttgattagg gtgatggttc acgtagtggg ggcggg                              36
```

```
<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
cttgattagg gtgatggttc acgtagtggg ggcggg                              36
```

```
<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
cttgattagg gtgatggttc acgtagtggg ggcgggaaaa aaaaaa                   46
```

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
gcccaggaag gaaggctgga agagtgcctc ggcggg                              36

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 21
gcccaggaag gaaggctgga agagtgcctc ggcggg                              36

<210> SEQ ID NO 22
<211> LENGTH: 46
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
gcccaggaag gaaggctgga agagtgcctc ggcgggaaaa aaaaaa                   46

<210> SEQ ID NO 23
<211> LENGTH: 46
<212> TYPE: RNA
<213> ORGANISM: Artificial Sequence
<220> FEATURE:
<223> OTHER INFORMATION: Description of Artificial Sequence:
      Oligonucleotide

<400> SEQUENCE: 23
cugggcaugg aguccugugg cauccacgaa acuaccuuca ggcggg                   46

<210> SEQ ID NO 24
<211> LENGTH: 46
<212> TYPE: RNA
<213> ORGANISM: Artificial Sequence
<220> FEATURE:
<223> OTHER INFORMATION: Description of Artificial Sequence:
      Oligonucleotide

<400> SEQUENCE: 24
cugggcaugg aguccugugg cauccacgaa acuaccuuca ggcggg                   46

<210> SEQ ID NO 25
<211> LENGTH: 55
<212> TYPE: RNA
<213> ORGANISM: Artificial Sequence
<220> FEATURE:
<223> OTHER INFORMATION: Description of Artificial Sequence:
      Oligonucleotide

<400> SEQUENCE: 25
cugggcaugg aguccugugg cauccacgaa acuaccuuca ggcgggaaaa aaaaa         55